US008523791B2

(12) United States Patent
Castel

(10) Patent No.: US 8,523,791 B2
(45) Date of Patent: Sep. 3, 2013

(54) MULTI-MODAL DRUG DELIVERY SYSTEM

(75) Inventor: J. Chris Castel, Reno, NV (US)

(73) Assignee: Laboratoire Naturel Paris, LLC, Reno, NV (US)

( * ) Notice: Subject to any disclaimer, the term of this patent is extended or adjusted under 35 U.S.C. 154(b) by 915 days.

(21) Appl. No.: 12/539,270

(22) Filed: Aug. 11, 2009

(65) Prior Publication Data

US 2011/0040235 A1 Feb. 17, 2011

(51) Int. Cl.
*A61H 1/00* (2006.01)
(52) U.S. Cl.
USPC .................................. 601/15; 610/46
(58) Field of Classification Search
USPC .................... 601/15, 46; 604/113; 607/3, 2
See application file for complete search history.

(56) References Cited

U.S. PATENT DOCUMENTS

| | | | |
|---|---|---|---|
| 1,968,686 A | 7/1934 | Janer | |
| 2,374,065 A | 4/1945 | Worthington | |
| 2,442,503 A | 1/1948 | Melnikoff | |
| 2,805,794 A | 9/1957 | Amon | |
| 3,677,654 A | 7/1972 | Davis | |
| 4,787,888 A | 11/1988 | Fox | |
| 5,117,478 A | 5/1992 | Cobb, Jr. et al. | |
| 5,169,384 A | 12/1992 | Bosniak et al. | |
| 5,309,544 A | 5/1994 | Saxe | |
| 5,415,629 A | 5/1995 | Henley | |
| 5,421,816 A | 6/1995 | Lipkovker | |
| 5,483,119 A | 1/1996 | Johanson | |
| 5,618,275 A | 4/1997 | Bock | |
| 5,656,016 A | 8/1997 | Ogden | |
| 5,658,892 A | 8/1997 | Flotte et al. | |
| 5,722,397 A | 3/1998 | Eppstein | |
| 5,772,347 A | 6/1998 | Gueret | |
| 5,814,599 A | 9/1998 | Mitragotri et al. | |
| 5,830,208 A | 11/1998 | Muller | |
| 5,932,240 A * | 8/1999 | D'Angelo et al. | 424/449 |
| 5,947,921 A | 9/1999 | Johnson et al. | |
| 6,041,253 A | 3/2000 | Kost et al. | |
| 6,187,029 B1 | 2/2001 | Shapiro et al. | |
| 6,251,099 B1 | 6/2001 | Kollias et al. | |
| 6,322,532 B1 | 11/2001 | D'Sa et al. | |
| 6,410,062 B1 | 6/2002 | Callaghan et al. | |
| 6,676,655 B2 | 1/2004 | McDaniel | |
| 6,689,094 B2 | 2/2004 | Kollias et al. | |
| 6,795,727 B2 | 9/2004 | Giammarusti | |
| 7,118,563 B2 | 10/2006 | Weckwerth et al. | |
| 7,458,982 B2 * | 12/2008 | Kraft et al. | 607/88 |
| 7,462,158 B2 | 12/2008 | Mor | |

(Continued)

FOREIGN PATENT DOCUMENTS

WO   WO 2008/114218      9/2008
WO   WO2008114218    *  9/2008

OTHER PUBLICATIONS

International Search Report and Written Opinion dated Nov. 9, 2010 for PCT/US2010/045120; 11 pages.

(Continued)

*Primary Examiner* — Michael A. Brown
(74) *Attorney, Agent, or Firm* — Stinson Morrison Hecker LLP

(57) ABSTRACT

A device for the transdermal delivery of a therapeutic agent at a treatment site comprising a housing containing: a mechanical vibration element; a light source; a heating and/or cooling element; a power source for powering said mechanical vibrational element, light source, and heating element; and an electronic control module.

91 Claims, 10 Drawing Sheets

(56) References Cited

U.S. PATENT DOCUMENTS

| | | | |
|---|---|---|---|
| 7,532,926 B2* | 5/2009 | Bernabei | 607/3 |
| 2001/0049546 A1 | 12/2001 | Dvoretzky et al. | |
| 2005/0208115 A1 | 9/2005 | Dvoretsky et al. | |
| 2006/0135911 A1* | 6/2006 | Mittur | 604/113 |

OTHER PUBLICATIONS

Kanikkannan et al., *Structure-activity Relationship of Chemical Penetration Enhancers in Transdermal Durg Delivery*, Curr. Med. Chemistry 6:7 593-608 (1999).

Mitragotri et al., *Synergistic Effect of Low-Frequency Ultrasound and Sodium Lauryl Sulfate on Transdermal Transport*, J. Pharm. Sci. 89:7 892-900 (2000).

Le et al., *Combined Effect of Low-Frequency Ultrasound and Iontophoresis: Applications for Transdermal Heparin Delivery*, Pharm. Res. 17:9 1151-1154 (2000).

Mitragotri, *Synergistic Effect of Enhancers for Transdermal Drug Delivery*, Pharm. Res. 17:11 1354-1359 (2000).

Mitragotri et al., *Transdermal Extraction of Analytes Using Low-Frequency Ultrasound*, Pharm. Res. 17:4 466-470 (2000).

Tezel et al., *Frequency Dependence of Sonophoresis*, Pharm. Res. 18:12 1694-1700 (2001).

Keyhani et al., *Intracellular Drug Delivery Using Low-Frequency Ultrasound: Quantification of Molecular Uptake and Cell Viability*, Pharm. Res. 18:11 1514-1520 (2001).

Tang et al., *Theoretical Description of Transdermal Transport of Hydrophilic Permeants: Application to Low-Frequency Sonophoresis*, J. Pharm. Sci. 90:5 545-568 (2001).

Barry, *Novel mechanisms and devices to enable successful transdermal drug delivery*, Eur. J Pharm. Sci. 14 101-114 (2001).

Mitragotri et al., *Transdermal Delivery of Hepoarin and Low-Moleculra Weight Heparin Using Low-Frequency Ultrasound*, Pharm. Res. 18:8 1151-1156 (2001).

Tezel et al., *A theoretical Analysis of Low-Frequency Sonophoresis: Dependence of Transdermal Transport Pathways on Frequecy and Energy Density*, Pharm. Res. 19:12 1841-1846 (2002).

Tang et al., *Effects of Low-Frequency Ultrasound on the Transdermal Permeationof Mannitol: Comparative Studies with In Vivo and In Vitro Skin*, J. Pharm. Sci. 91:8 1776-1794 (2002).

Terahara et al., *Dependence of low-frequency sonophoresis on ultrasound parameters; distance of the horn and intensity*, Int'l J. of Pharmaceutics 235 35-42 (2002).

Kanikkannan, *Iontophoresis-Based Transdermal Delivery Systems*, Biodrugs 16:5 339-347 (2002).

Tezel et al., *Investigations of the Role of Cavitation in Low-Frequency Sonophoresis Using Acoustic Spectroscopy*, J. Pharm. Sci. 91:2 444-453 (2002).

Tezel et al., *Synergistic Effect of Low-Frequency Ultrasound and Surfactants on Skin Permeability*, J. Pharm. Sci. 91:1 91-100 (2002).

Terahara et al., *Porous Resins as a Cavitation Enhancer for Low-0Frequency Sonophoresis*, J. Pharm. Sci. 91:3 753-759 (2002).

Tang et al., *Prediction of Steady-State Skin Permeabilities of Polar and Nonpolar Permeants across Excised Pig Skin Based on Measurements of Transient Diffusion: Characterization of Hydration Effects on the Skin Porous Pathway*, J. Pharm. Sci. 91:8 1891-1907 (2002).

Tang et al., *An Investigation of the Role of Cavitation in Low-Frequency Ultrasound-Mediated Transdermal Drug Transport*, Pharm. Res. 19:8 1160-1169 (2002).

Tezel et al., *Description of Transdermal Transport of Hydrophilic Solutes during Low-Frequency Sonophoresis Based on a Modified Porous Pathyay Model*, J. Pharm. Sci. 92:2 381-393 (2003).

Nokhodchi et al., *The enhancement effect of surfactants on the penetraton of lorazepam through rat skin*, Int'l J. of Pharm. 250 359-369 (2003).

Tezel et al., *Interactins of Inertial Cavitation Bubbles with Stratum Corneum Lipid Bilayers during Low-Frequency Sonophoresis*, Biophysical Jour. 85 3502-3512 (2003).

Mitragotri et al., *Low-frequency sonophoresis—A review*, Adv. Drug Delivery Reviews 56 589-601 (2004).

Langer, *Transdermal drug delivery: past progress, current status, and future prospects*, Adv. Drug Delivery Reviews 56 557-558 (2004).

Lavon et al., *Ultrasound and transdermal drug delivery*, DDT 9:15 670-676 (2004).

Kalia et al, *Iontophoretic drug delivery*, Adv. Drug Delivery Rev. 56 619-658 (2004).

Doukas et al., *Transdermal drug delivery with a pressure wave*, Adv. Drug Delivery Rev. 56 559-579 (2004).

Mitragotri, *Breaking the Skin Barrier*, Adv. Drug Delivery Rev. 56 555-556 (2004).

Santoianni et al., *Intradermal drug delivery by low frequnecy sonophoresis (25KHz)*, Dermatology Onine 10:2 (2004).

Cross et al., *Physical Enhancement of Transdermal Drug Application: Is Delivery Technology Keping up with Pharmacedutical Development?*, Curr. Drug Delivery 1:1 81-92 (2004).

Tezel et al., *Topical Delivery of Anti-sense Oligonucleotides Using Low-Frequency Sonophoresis*, Pharm. Res. 21:12 2219-2225 (2004).

Benson, *Transdermal Drug Delivery: Penetration Enhancement Techniques*, Curr. Drug Delivery 2:1 23-33 (2005).

Nanda et al., *Current Developments Using Emerging Transdermal Technologies in Physical Enhancement Methods*, Curr. Drug Delivery 3 233-242 (2006).

Brown et al., *Dermal and Transdermal Drug Delivery Systems: Current and Future Prospects*, Drug Delivery 13 175-187 (2006).

\* cited by examiner

MULTI-MODAL DRUG DELIVERY SYSTEM

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates to transdermal drug delivery device and method, most preferably for the delivery of Vitamin C (ascorbic acid), using a combination of light therapy, heat therapy, cold therapy, and ultrasound therapy.

2. Description of Related Art

The process of wound healing generally encompasses three phases during which the injured tissue is repaired, regenerated, and new tissue is reorganized into a scar. These three phases are classified as: (a) an inflammation phase which begins from about day 0 to 3 days, (b) a cellular proliferation phase from about 3 to 12 days, and (c) a remodeling phase from about 3 days to about 6 months. In all three phases, antioxidants, such as Vitamin C, play a vital role in the healing process.

In the inflammation phase, inflammatory cells, mostly neutrophils, enter the site of the wound followed by lymphocytes, monocytes, and later macrophages. The neutrophils that are stimulated begin to release proteases and reactive oxygen species into the surrounding medium with potential adverse effects on both the adjacent tissues and the invading microorganisms.

The proliferative phase consists of laying down new granulation tissue, and the formation of new blood vessels in the injured area. The fibroblasts, endothelial cells, and epithelial cells migrate in the wound site. These fibroblasts produce the collagen that is necessary for wound repair. Ascorbic acid is crucial in the formation of collagen. Several studies have demonstrated that ascorbic acid is capable of overcoming the reduced proliferative capacity of elderly dermal fibroblasts, as well as increasing collagen synthesis in elderly cells by similar degrees as in newborn cells even though the basal levels of collagen synthesis are age dependent. A decrease of ascorbic acid at the injury area will decrease the rate of wound healing.

The final phase of wound healing, which is remodeling, is effected by both the replacement of granulation tissue with collagen and elastin fibers and the devascularization of the granulation tissue. Recent studies have shown that topical application of antioxidants reduces scarring and normalizes blood coagulation during therapy.

The present invention is directed to an improved delivery device and method for the transdermal administration of various therapeutic agents, including therapeutic agents useful in the various phases of wound healing, such as ascorbic acid. The device incorporates the use of mechanical or vibrational energy (most preferably ultrasound), light therapy (most preferably near-infrared light therapy), and heat and/or cold therapy as part of the wound healing process.

BRIEF SUMMARY OF THE INVENTION

The present invention is directed to a device for the transdermal delivery of a therapeutic agent at a treatment site and methods of using the device. In general, the device comprises a housing containing a mechanical vibration element, a light source, a heating and/or cooling element, a power source for powering the mechanical vibration element, light source, and heating/cooling element. An electronic control module is used to control the mechanical vibration element, light source, and heating and/or cooling element.

In another aspect, the mechanical vibration element, light source, and heating and/or cooling elements are positioned within an injection molded housing. The housing may optionally contain a reservoir having a therapeutic composition therein. A preferred active agent in the therapeutic composition is ascorbic acid and its pharmaceutically acceptable salts and esters. A piston may be positioned in the reservoir and adapted to dispense the therapeutic composition from the housing. The therapeutic composition may also be contained in a replaceable cartridge or pouch in the reservoir.

In one aspect, the mechanical vibration element comprises one or more of an ultrasonic transducer, motor having an offset cam, buzzer, voice coil, or magnetic transducer, or combinations thereof. The mechanical vibration element preferably has an operating frequency of between about 15 kHz and 35 kHz. In another aspect, the mechanical vibration element produces mechanical energy having a frequency of about 100 kHz to 5 MHz, preferably in the range of 500 kHz to 1 MHz modulated with mechanical energy having a frequency of about 15 kHz to 100 kHz. In still another aspect, mechanical vibration element produces mechanical energy having a frequency of about 10 Hz to 1000 Hz modulated with mechanical energy having a frequency of about 15 kHz to 100 kHz.

In still another aspect, the light source produces light having a wavelength between about 600 nm and 1650 nm. The light source is optionally modulated with a light modulation frequency, for example, light energy pulsed at frequency between about 15 kHz and 100 kHz. In a preferred embodiment, the light modulation frequency is synchronized with the mechanical energy modulation frequency. The light source may comprise one or more light emitting diodes, a laser, a non-scanning laser, a light ring, or combinations thereof. The light sources may also be superimposed on one another.

In still another aspect, the mechanical vibration element and the light source are operated in different frequencies or wavelengths during the treatment regimen. For example, the mechanical vibration element may operate at a first modulation frequency for a first period of time followed by a second modulation frequency for a second period of time. Likewise, light source may be pulsed at a first modulation frequency for a first period of time followed by a second modulation frequency for a second period of time.

In still another aspect, the heating and/or cooling element comprises a Peltier element, resistor, or combinations thereof. The Peltier element is preferably positioned annularly around mechanical vibration element, such as the ultrasonic transducer.

In still another aspect, the present invention is directed to a method for transdermally delivering a therapeutic agent (such as ascorbic acid) to a patient's treatment site by: decreasing the temperature of the treatment site by cooling the treatment site; increasing the temperature of the treatment site by heating the treatment site by about 0.5 to 2° C.; or increasing the temperature of the treatment site by heating the treatment site by about 2 to 4° C.—depending on the desired therapeutic outcome. Further, the method includes the steps of applying mechanical energy the treatment site, wherein the mechanical energy has a frequency of about 15 kHz to 100 kHz; applying light energy to the treatment site; and applying a composition comprising a therapeutically effective amount of the therapeutic agent. These steps may be preformed in separately, but are preferably performed simultaneously.

In one aspect, the applying mechanical energy step comprises applying mechanical energy having a high frequency of about 100 kHz to 5 MHz modulated with mechanical energy having a frequency of about 15 kHz to 100 kHz. In another aspect, the applying mechanical energy step comprises applying mechanical energy having a frequency of about 10 Hz to 1000 Hz modulated with mechanical energy having a frequency of about 15 kHz to 100 kHz. In another aspect, the applying light energy step comprises applying light having a wavelength between 600 nm and 1650 nm and modulated with a light modulation frequency, preferably one that that is synchronized with the mechanical energy modulation frequency. The frequencies and wavelengths of the mechanical energy and the light energy may be varied over the treatment course in order to optimize the transdermal delivery of the various therapeutic agents in the composition. Thus, in one aspect, the mechanical energy is applied at a first frequency associated with delivery of a first therapeutic agent to the treatment site, and the mechanical energy is then applied at a second frequency associated with delivery of a second therapeutic agent to the treatment site, and wherein the first frequency and the second frequency are different. The frequencies may be determined by microdialysis. Microdialysis allows the measurement of penetration of a given therapeutic agent subcutaneously, and as such, can be used to optimize the frequencies to be used for a specific therapeutic agent.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1:
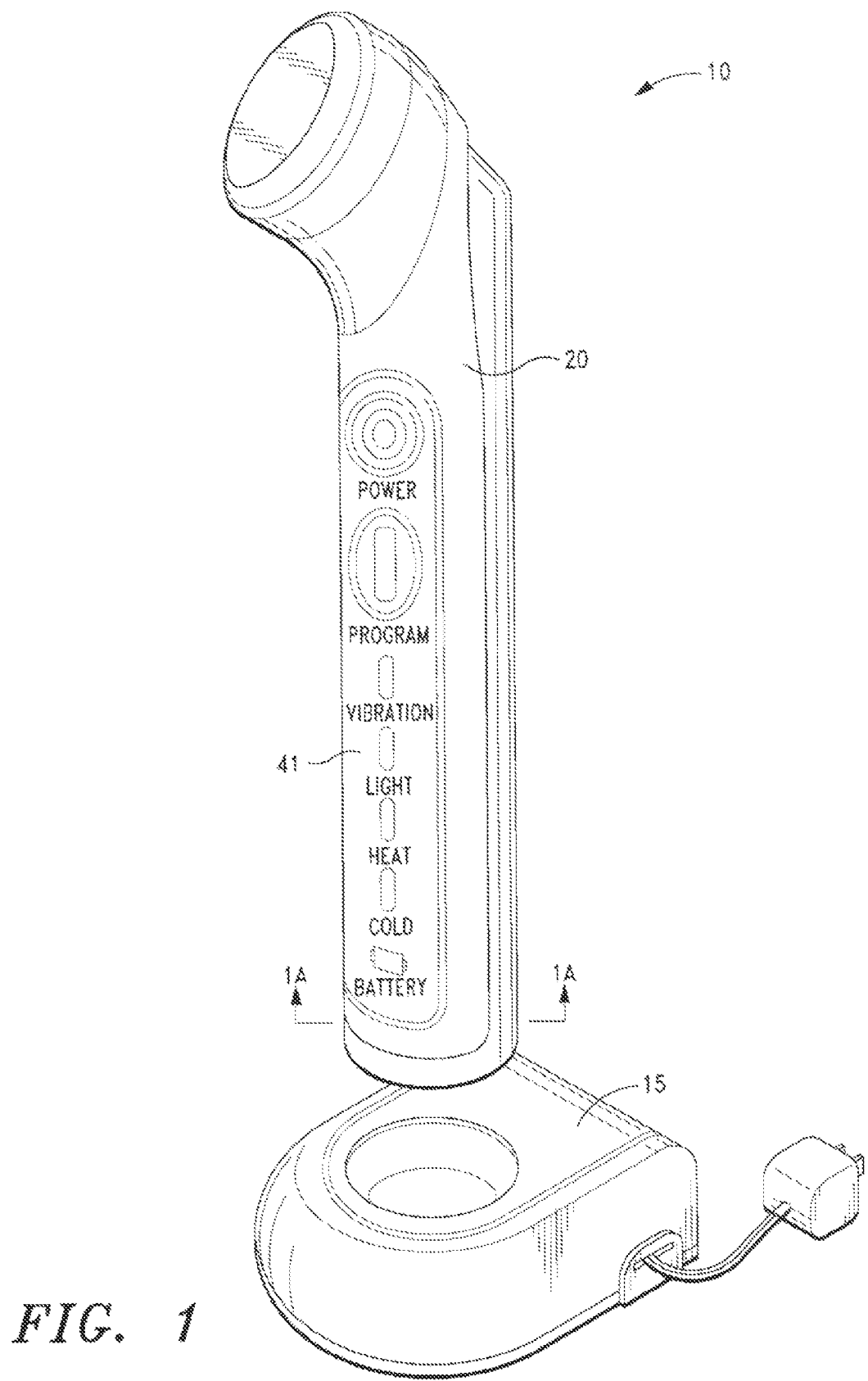
FIG. 1 is a perspective view of a multi-modal device for the deli very of a topical therapeutic agent in accordance with a first embodiment of the present invention.

The present invention is directed to a device and method for the delivery of a therapeutic agent, preferably ascorbic acid, through a biological membrane, such as the skin. The device is capable of operating in at least two modes. In one modality, the device provides vibration or mechanical energy (e.g., ultrasound), light energy (e.g., near-infrared LEDs and/or lasers), and cooling (e.g., via a Peltier element). In this mode, it is theorized that mechanical vibration causes cavitation effects which assist in the movement of the ascorbic acid through the skin. The light energy is delivered at a level that triggers the degranulation of mast cells to trigger the inflammatory phase of healing, but does not increase the overall tissue temperature. The cooling decreases blood flow and reduces inflammation. Cold is known to relieve pain and inflammation by its direct effects on circulation and metabolism. A reduction in temperature to any injured body part, whether minor or acute, causes blood vessels and blood cells in the area of trauma to shrink in size, thus slowing the flow and rush of fluids into areas of irritated tissue. This decrease in swelling and inflammation in turn reduces pain and accelerates the inflammatory phase of healing. The device is operated such that it cools the treatment site. In one aspect, the light source (near-infrared LEDs and/or lasers) and mechanical energy source (the ultrasound) are operated at power levels that do not change the temperature of the treatment site.

In a second modality, the device provides mechanical vibration (e.g., ultrasound), light energy (e.g., near-infrared LEDs and/or lasers), and mild heating of about 1-2° C. (e.g., via a Peltier element, the light energy, resistive heating elements, or combinations thereof. It is theorized that mechanical vibration causes cavitational effects which assist in the movement of the ascorbic acid through the skin. The light energy triggers the collagen regeneration and production by activation of fibroblasts. The device is operated such that it provides mild to moderate heat to the treatment site. In one aspect, the light source (near-infrared LEDs and/or lasers) and mechanical energy source (the ultrasound) are operated at power levels that cause the temperature of the treatment site to increase about 1-2° C. A Peltier element, resistor, or other thermal device could also be used to provide the desired temperature change.

In a third modality, the device provides mechanical vibration (e.g., ultrasound), light energy (e.g., near-infrared LEDs and/or lasers), and vigorous heating of about 2-4° C. (e.g., via a Peltier element, the light energy, resistive healing elements, or combinations thereof. It is theorized that mechanical vibration causes cavitational effects which assist in the movement of the ascorbic acid through the skin. The heating increases blood flow and assists in collagen remodeling. The device is operated such that it provides vigorous heal to the treatment site. In one aspect, the light source (near-infrared LEDs and/or lasers) and mechanical energy source (the ultrasound) are operated at power levels that cause the temperature of the treatment site to increase about 2-4° C. A Peltier element, resistor, or other thermal device could also be used to provide the desired temperature change.

The treatment time may vary depending upon the therapeutic agent being delivered to the treatment site. Typically, the treatment time ranges between 30 seconds and 30 minutes. The device is preferably equipped with an audio or visual alert that informs the user when the treatment time has been met. For example, when applying ascorbic acid to the face, the user will typically move the device over the facial structures to be treated. The device may alert the user when the device has been applied at a particular location on the face after, for example, 30 seconds. The user may then move the device to another area of the face for treatment for another 30 seconds (or some other desired time), at which point the alert is activated again. In addition, the alert may also tell the user when the frequencies (and/or modulation frequencies) should be changed in order to maximize the transport of each therapeutic agent into the skin.

The device is preferably a non-invasive cordless, self-contained device. Thus, while the device may be electrically plugged into an external outlet or power source during use, the device is preferably battery-powered. Further, the device is preferably not physically connected to a base unit or other such unit and is free to be manipulated without attached wires or couplings during use, and is free of externally protruding physical couplings, such as control wires, optical cables, and power cords.

As used herein, "individual" or "patient" refers to a human, to which the present invention may be applied.

As used herein, the "treatment site" refers to the surface of a patient's skin. The treatment site may be healthy tissue or comprise a wound, including a wound in any stage of healing.

The Housing and Cap Assembly

The inventive device comprises a housing for containing the mechanical vibration element, the light source, and heating and/or cooling element. The housing optionally contains a therapeutic agent suitable for transdermal delivery.

The transdermal drug delivery device is typically no larger than a standard tube of lipstick or a cigar tube. In one aspect, the device has a volume less than approximately 20 cm$^3$, and more preferably less than approximately 10 cm$^3$, and a weight less than approximately 50 g, preferably less than about 20 g. The device can be gripped and firmly controlled in a self-care procedure within a user's hand. While the housing is generally shown as being tubular or cylindrical in shape, the housing can be any suitable shape. The housing is preferably made from a polymer, metal, ceramic, or other suitable material.

As discussed more fully below with respect to the exemplary embodiments, the housing has a first end and a second end. The power source for the device and an electronic control unit are preferably positioned at the first end, while the mechanical vibration element, light source, and heating and/or cooling elements are preferably positioned at the second end.

Various power sources are known in the art. The preferred power source for the device includes those that are used with many portable consumer devices, including palm-sized computers, games, flashlights, shavers, radios, CD players, phones, power tools, small appliances, tooth brushes, etc. For example, the power source may comprise a "contactless" or inductive battery-charging system. There are generally of two types-inductive charging systems and infrared charging systems. Inductive charging systems include an electromagnetic or radio frequency coil that generates an electromagnetic field, which is coupled to a receiver coil within the device that includes a battery requiring recharging. For use in recharging a battery in a handheld powered toothbrush, a relatively high-frequency current is supplied to the transmitter coil in a base for the handheld toothbrush, thereby generating a varying magnetic field at a corresponding frequency. This magnetic field is inductively coupled to a receiver coil in the toothbrush housing to generate a battery charging current. See, e.g., U.S. Pat. No. 3,938,018 "Induction Charging System"; U.S. Pat. No. 5,959,433 "Universal Inductive Battery Charger System"; U.S. Pat. No. 4,873,677 "Charging Apparatus for an Electronic Device"; and U.S. Pat. No. 5,952,814 "Induction Charging Apparatus and an Electronic Device." A different contactless system for charging batteries is an infrared charging system employing a light source as a transmitter and a photocell as a receiver. Energy is transferred from the source to the receiving photocell via light rather than through a magnetic field.

It will be appreciated to those skilled in the art that other power sources may be employed. For example, conventional disposable or rechargeable batteries, including but not limited to nickel-cadmium, lead-acid, nickel-metal-hydride, or lithium-ion type batteries. As another example, the power source may also comprise a conventional charge-conditioning circuit (either internally or externally) that can be used with a conventional power source, such as a wall outlet, to provide a conditioned direct current (DC) at a voltage suitable for recharging a battery contained in the device. For example, it is common for electric shavers to include a charge-conditioning circuit that enables a nickel-cadmium (or other type) battery retained in the shaver to be recharged by plugging the shaver into a line voltage outlet. Similarly, some flashlights have an integrated connector that allows them to be recharged by simply plugging them into a wall outlet. In addition, certain devices such as portable hand vacuum cleaners use a "base" charger unit for both storing the device between uses and recharging the battery. When the portable device is stored in the base unit, exposed terminals on the device are connected through contacts on the base unit to a power supply energized with line current, thereby providing a conditioned DC current to charge the battery within the portable device.

The second end of the housing is adapted to be applied to a patient's skin to facilitate the transdermal delivery of a therapeutic agent (either contained within the housing or applied from an external source) at a treatment site.

In one aspect, the second end of the housing has a cap assembly formed of glass, ceramic, or metal or plastic, or other suitable material. The glass or plastic cap assembly is fully or partially transmissive (e.g., 20, 30, 40, 50, 60, 70, or 80% transmissive) and is preferably etched with a pattern to allow light to be applied to the treatment site in pre-determined patterns. The pre-determined pattern is generally based on the location of the light source, the nature of the etched surface, and in the case of a laser as the light source, the scanning pattern of the laser as discussed more fully below. The etching or pattern may be optimized for light transmission and heat generation on the transducer surface. In one aspect, the pattern disperses the light so that the transducer surface heats evenly. The preferred pattern is a continuous raster scan or a dot pattern over the transducer surface. Scan speeds and dot size can also be varied to produce the appropriate depth of penetration of the lasers.

As discussed in some of the exemplary embodiments below, an ultrasonic transducer may be mounted directly on the cap assembly so that mechanical energy can be applied to the treatment site. The proximity of the light source (e.g., the LEDs and/or laser) to the surface of the cap assembly may also be adjusted to provide varying degrees of heat to the cap assembly. In one aspect, the cap assembly preferably forms the treatment transducer surface with the light source (e.g., the LED and/or lasers) mounted behind the cap assembly.

For devices containing a therapeutic agent, the cap assembly is further provided with one or more openings for delivery of the therapeutic agent to the treatment site. Most preferably, the openings engage corresponding delivery tubes which lead to a reservoir that contains the therapeutic agent. The reservoir may be equipped with a plunger that is actuated to deliver the therapeutic agent to the treatment site. Alternatively, the reservoir may be comprised of a flexible material so that when pressure is applied to the flexible internal container (e.g., by a plunger or manual compression), the therapeutic agent is forced through the delivery tubes into the openings for delivery of the therapeutic agent to the treatment site.

Mechanical/Vibrational Energy (Ultrasound)

The device includes a mechanical vibration element for delivering low frequency mechanical/vibrational energy to the treatment site. As used herein, the term "low frequency" refers to that which is less than about 5 MHz, more preferably less than about 1 MHz, 100 kHz, or 50 kHz, and most preferably less than about 35 kHz. Preferred low frequency ranges are about 15 kHz to 100 kHz, about 15 kHz to 50 kHz, and most preferably about 15 kHz to 35 kHz. As discussed below in one aspect, low frequency or high frequency mechanical vibrations can be modulated with lower or higher frequencies in order to provide lower and higher frequency harmonics. The modulation may be performed continuously or in steps, and for different amounts of time.

The mechanical/vibrational energy is preferably produced using an ultrasonic transducer, a voice coil, a buzzer, a magnetic transducer, or a motor having an offset cam. When voice coils, buzzers, magnetic transducers, and motors are used in the device, they are preferably mounted so that they contact (either directly or indirectly) the interior wall of the housing such that the mechanical energy produced by such devices is transferred through the housing to the treatment site. An exemplary motor is commercially available from Thomson, A Danaher Motion Company (Wood Dale, Ill.). The housing is preferably tuned to maximize the resonance of the transducers. Thus, the housing is designed to acoustically amplify the resonance peaks of the desired treatment frequencies, much like the sound box of a musical instrument. The transducer is preferably mounted so that the vibration is provided in the same plane as the outer transducer surface.

The ultrasonic transducer is typically either a piezoelectric, ceramic, or polymer block. Most preferably, the ultrasonic transducer is a piezoelectric transducer for delivering low-frequency ultrasound energy. The transducer is preferably mounted or otherwise directly positioned at one end of the housing near the cap assembly so that the mechanical energy is transferred from the transducer through the cap assembly to the treatment site. The ultrasonic transducer may be positioned against the walls of the housing so that the vibration is transmitted to the treatment site when the device is in use. The ultrasonic transducer is powered by the power source and controlled by the electronic control module.

It will be appreciated that the low frequency waves of the ultrasonic transducer may be produced by using a commercially available therapeutic transducer, preferably in the range of about 100 kHz to 5 MHz, and more preferably in the range of about 500 kHz to 1 MHz (typically about 1 MHz) which is applied in modulated bursts, at a 1-99% duty cycle at a burst rate of about 10 kHz to 100 kHz, and preferably such that the pulse burst shape optimizes the targeted low frequency harmonics. The intensity of the ultrasound is preferably in the range of between about zero and 3.0 W/cm$^2$, more typically between about about 5 mW/cm$^2$ and 200 mW/cm$^2$. Exposures to the treatment site are typically for between about 1 and 15 minutes, but may be shorter and/or pulsed. Other ultrasonic transducer parameters including, but not limited to, amplitude, duty cycle, distance from the treatment site, and application time may be varied to achieve sufficient enhancement of transdermal transport. The pressure amplitude may be varied from above about zero to 50 kPa. The duty cycle can vary from between about 1% and 100%. The transducer is generally positioned at a distance from the treatment site between about 0.1 mm and 5 mm.

In another aspect, the device produces vibration of about 10 Hz to 1000 Hz preferably about 10 Hz to 100 Hz, more preferably about 10 Hz to 50 Hz, and most preferably about 15 Hz to 30 Hz, using a voice coil, buzzer, motor with an offset cam, or magnetic transducer, which is felt on the transducer surface, and can be tuned using pulse modulated currents to optimize higher frequency harmonics in the range of about 15 kHz to 100 kHz, more preferably about 15 kHz to 50 kHz, and most preferably about 15 kHz to 35 kHz.

Many ultrasonic devices are available commercially which can be used in the device described herein. For example, the ultrasonic devices used by dentists to clean teeth have a frequency of between about 25 kHz and 40 kHz. Commercially available portable ultrasonic tooth-brushes make use of a small sonicator contained within the tooth-brush (Sonex International Corporation). This sonicator is portable and operates on rechargeable batteries.

The mechanical/vibrational energy provides cavitational effects in the skin, which improves drug delivery into and through the skin. As such, application of low-frequency (e.g., about 15 kHz to 100 kHz) mechanical/vibrational energy dramatically enhances transdermal transport of drugs. Cavitation may cause disordering of the stratum corneum lipids. In addition, oscillations of cavitation bubbles may result in significant water penetration into the disordered lipid regions. This may cause the formation of aqueous channels through the intercellular lipids of the stratum corneum. This allows permeants to transport across the disordered lipid domains, then across keratinocytes and the entire stratum corneum. This transport pathway may result in an enhanced transdermal transport as compared to passive transport because the diffusion coefficients of permeants through water, which is likely to primarily occupy the channels generated by ultrasound, are up to 1000-fold higher than those through the ordered lipid bilayers, and the transport path length of these aqueous channels may be much shorter (by a factor of up to 25) than that through the tortuous intercellular lipids in the case of passive transport.

It will be appreciated the mechanical vibration energy element of device may be operated at different frequencies in order to maximize transport of various therapeutic agents in a composition. For example, it will be appreciated that therapeutic agent "A" may be optimally transported at frequency $\omega_A$ with an optional modulation frequency $\omega_{MA}$ while therapeutic agent "B" may be optimally transported at frequency $\omega_B$ with an optional modulation frequency $\omega_{MB}$. The different frequencies (and optional modulation frequencies) result in different cavitation effects and create different sizes of distortions in the strateum corneum, allowing different sizes of molecules and compounds to pass through the skin. Thus, the present invention contemplates that the frequencies and/or the modulation frequencies can be varied continuously or in stages during operation. That is, the present invention contemplates that the mechanical vibration element can operate at multiple frequencies (e.g., continuously over a selected range of frequencies or at one or more pre-determined frequencies). Further, the device may be programmed using the electronic control module to operate in cycles of different frequencies that correspond to those associated with the various therapeutic agents. For example, the device may be programmed to operate at a frequency $\omega_A$ for a First period of time (in order to maximize transport of therapeutic agent A) and then operate at a frequency $\omega_B$ for a second period of time (in order to maximize transport of therapeutic agent B). As another example, the device may be programmed to operate at a frequency $\omega_A$ with a modulation frequency of coma for a first period of time (in order to maximize transport of therapeutic agent A) and then operate at a frequency $\omega_B$ with a modulation frequency $\omega_{MB}$ for a second period of time (in order to maximize transport of therapeutic agent B). As yet another example, the device may be operated at a frequency $\omega_A$ with a modulation frequency of $\omega_{MA}$ for a first period of time followed by a change in the modulation frequency only to $\omega_{MB}$ for a second period of time. The cycling and patterns of the frequency provides significant benefits in transporting compositions containing multiple therapeutic agents through the skin surface. The amount of time at each frequency may also be programmed into the electronic control module based on the percentage composition of the therapeutic agent and the diffusion rate through the skin for the therapeutic agent. It will be appreciated that multiple therapeutic agents may be delivered using similar and techniques to optimize each therapeutic agent.

Light Energy

The device of the present invention also comprises a single or multiple near infrared light sources. The light source is preferably a set of LEDs or lasers for delivering near-infrared light, preferably having wavelengths from about 600 nm to 1650 nm, preferably about 600 nm to 650 nm, and most preferably about 630 nm. Typically, the light source operates at an average power of about 5 mW to 100 mW or at energy densities of about 1 to 20 J/cm². It is anticipated that the light energy provides synchronized shock waves and/or heat to the tissue surface to drive drug molecules into and through the skin at the treatment site by increased diffusion. The light has a phototherapeutic effect by increasing blood flow and collagen synthesis.

In one exemplary embodiment, a plurality of LEDs are positioned in an annular pattern at the periphery at one end of the device. For devices using an ultrasonic transducer, the plurality of LEDs are preferably positioned around the ultrasonic transducer. Pre-determined etched patterns on a light-conductive cap plate assembly may be included in order to help direct the light in the appropriate plane and location at the treatment site. The pattern, for example, may be circular, oval or grid pattern, or any other pattern designed to provide an even dispersion of the light to the treatment site.

In another exemplary embodiment, a scanning laser is positioned in the housing. The laser is programmed by the electronic control module to scan in pre-determined patterns. The patterns include continuous raster scan or dot patterns over the transducer surface. The scan speeds and dot size can be varied to produce the appropriate depth of penetration of the laser. Typically, the laser is positioned in the housing so that the light energy can be transmitted through the cap assembly without interference from the other elements of the device (e.g., the heating/cooling element, the mechanical vibration element, and/or the LEDs).

In another aspect, a non-scanning laser and/or LEDs transmit light to a light pipe or light tube. Such devices distribute light over their entire length, either for equidistribution of the light along the entire length, or for controlled light leakage. Numerous light pipes are commercially available. See Cobb Jr. et al, U.S. Pat. No. 5,117,478; Johanson, U.S. Pat. No. 5,483,119; and Saxe U.S. Pat. No. 5,309,544. A preferred light pipe is manufactured by the Visual Communications Company (San Marcos, Calif.). In general, light from the LEDs and/or lasers is transferred via a fiber optics cable to the light pipe. The light pipe can have any suitable shape or configuration, but it preferably forms an annular ring so that the light is distributed in corresponding annular fashion to the treatment site. Further, the light pipe is preferably constructed so that light is directed in towards the pretreatment site and the light is not disseminated into the device itself.

In one aspect, the lasers and/or LEDs are pulsed at various frequencies, including the modulation or fundamental frequencies of the ultrasonic transducer. The pulsation is preferably synchronized to maximize cavitation effects on the cellular membranes and the stratum corneum. The wavelength of the light is selected to optimize the healing and biostimulative effects in the tissue and the light modulation frequencies arc synchronized with the frequencies of the mechanical/vibrational energy (ultrasonic) modulation or the fundamental frequency of the ultrasonic transducer (in the case of a low frequency ultrasonic transducer). This synergistic effect enhances the shear waves and cavitation effects in the tissue when the laser and/or LEDs are pulsed synchronously with the ultrasonic wave modulation.

Thus, it will be appreciated the light energy element of device may be operated at different wavelengths modulated at different frequencies in order to maximize transport of various therapeutic agents in a composition. For example, it will be appreciated that therapeutic agent "A" may be optimally transported at light wavelength $\lambda_A$ and pulsed with an optional modulation frequency $\omega_{MA\text{-}Light}$ while therapeutic agent "B" may be optimally transported at frequency $\lambda_B$ with an optional modulation frequency $\omega_{MB\text{-}Light}$. The different wavelengths (and optional modulation frequencies) result in different cavitation effects and create different sizes of distortions in the strateum corneum, allowing different sizes of molecules and compounds to pass through the skin. Thus, the present invention contemplates light having various wavelengths and the modulation frequencies can be varied continuously or in stages during operation. That is, the present invention contemplates that the light source can operate at multiple wavelengths (e.g., continuously over a selected range of wavelengths or at one or more pre-determined wavelengths). Further, the device may be programmed using the electronic control module to operate in cycles of different wavelengths that correspond to those associated with the various therapeutic agents. For example, the device may be programmed to operate at a wavelength $\lambda_A$ for a first period of time (in order to maximize transport of therapeutic agent A) and then operate at a wavelength $\lambda_B$ for a second period of time (in order to maximize transport of therapeutic agent B). As another example, the device may be programmed to operate at a wavelength $\pi_A$ with a modulation frequency of $\omega_{MA\text{-}Light}$ for a first period of time (in order to maximize transport of therapeutic agent A) and then operate at a wavelength $\lambda_B$ with a modulation frequency $\omega_{MB\text{-}Light}$ for a second period of time (in order to maximize transport of therapeutic agent B). As yet another example, the device may be operated at a wavelength $\lambda_A$ with a modulation frequency of $\omega_{MA\text{-}Light}$ for a first period of time followed by a change in the modulation frequency only to $\omega_{MB\text{-}Light}$ for a second period of time. The cycling and patterns of the light energy wavelengths and modulation frequencies provides significant benefits in transporting compositions containing multiple therapeutic agents through the skin surface. The amount of time at each wavelength and/or modulation frequency may also be programmed in to the electronic control module based on the percentage composition of the therapeutic agent and the diffusion rate through the skin for the therapeutic agent.

In another aspect, the LEDs operate continuously to cause an increase in tissue temperature, thus increasing the cellular diffusion rate. A laser signal is then superimposed operating in a pulsed mode (e.g., a frequency of about 15 kHz to 100 kHz) which is synchronized with the ultrasonic modulation frequency to enhance cavitation and shear-wave production. These configurations are designed to enhance the penetration of substances, molecules, and compounds as a result of the increased temperature and enhanced cavitation effects when synchronized with the mechanical vibrations from the ultrasonic generators and/or the mechanical vibrators. The modulation frequency scanning of the lasers and LEDs in discrete steps or continuously provides significant benefits in transporting solutions containing multiple compounds through the skin surface. The frequency components of the ultrasound shear-wave and light pulses produce different sized cavitation bubbles that can allow the selective transfer of differing sizes of molecules through the skin.

To ascertain the appropriate modulation of high frequency ultrasound or the fundamental frequency of low frequency ultrasound for a given therapeutic agent, microdialysis can be used. Likewise, the effects of pulsing the light at various modulation frequencies may also be determined. In general, a composition containing the therapeutic agent is placed on the tissue surface in a conductive ultrasound gel. The ultrasonic transducer is placed over the gel and the issue and activated at the appropriate dose and test frequency. Sterile water is pumped through a microdialysis probe implanted approximately 2 mm under the skin under the transducer. See, e.g., Klimowiez, *Evaluation of Skin Penetration of Topically Applied Drugs in Humans by Cutaneous Microdialysis*, J Clin Pharm Ther. Apr.; 32 (2): 143-8 (2007); and Ault et al., *Microdialysis Sampling for the Investigation of Dermal Drug Transport*, Pharm Res. Oct. 9 (10):1256-61 (1992), both of which are incorporated by reference. Exemplary ranges of test frequencies for delivery of vitamin C (ascorbic acid) in a carrier composition comprising are provided below:

Test No. 1:
Vitamin C, 25 wt % in an aqueous gel
Ultrasonic transducer frequency: 1 MHz
Modulation frequency of ultrasound: 10 kHz to 100 kHz
Light wavelength: 600 nm to 650 nm
Modulation frequency of light: 10 kHz to 100 kHz
Treatment time: 30 minutes Frequency ranges and duration that each frequency that have optimized transdermal delivery for each therapeutic agent and are be programmed into the controller. Thus, it is contemplated that the device applies a frequency (mechanical vibration and/or light) for each therapeutic agent. That is, assuming that the transdermal delivery of therapeutic agent A is optimal at a first ultrasonic frequency $\omega_A$ (with an optional modulation frequency $\omega_{MA}$) and a first light wavelength $\lambda_A$ (with pulsing at an optional light modulation frequency of $\omega_{MB-Light}$) and the transdermal delivery of therapeutic agent B is optimal at a second ultrasonic frequency $\omega_B$ (with an optional modulation frequency $\omega_{MB}$) and a second light wavelength $\lambda_B$ (with pulsing at an optional light modulation frequency of $\omega_{MB-Light}$) then the device is programmed to operate in at least both modalities. In one aspect, the mechanical vibration and light are modulated at the same frequency.

The use of a near-infrared light source enables the device to apply therapeutic
thermal treatment as well as photo-treatment by facilitating a localized increase in skin temperature. In a preferred embodiment, it is anticipated that the light source will elevate the skin temperature elevation about 2 to 4° C. (e.g., to about 41° C.).

As a result of the wavelength of the light, and the frequency of pulsation, and the energy delivery from the light source, there results in the body a large number of physiologic responses. These physiological responses include, for example, acceleration of the production of procollagen resulting in enhanced collagen synthesis through selective action on collagen gene expression at the transcriptional level. This is a likely sequel to elevations of procollagen mRNA levels resulting in alterations in the chromatin structure. There is also theorized to be increased cross-linking of existing collagen molecules and improved organization of functional collagen fibers. Also, it is theorized that the device stimulates macrophages (a type of white blood cell) to release factors that stimulate fibroblast replication and proliferation (e.g., monokines). Cellular effects which occur include mitochondrial hyperplasia, the appearance of cytoplasmic microfilament bundles, and the deposition of an abundant fibrillar matrix in pericellular regions. A cellular phenotype of the fibroblast, the myofibroblast, is generated. This cell is found in granulation tissue; and its primary role occurs in the remodeling phase of wound healing, including contractile activity in addition to the synthesis of collagen. The photothermal treatment device thereby accelerates the formation of a functional scar. See generally, Shapiro, U.S. Pat. No. 6,187,029.

Temperature Control Element

To provide additional heating or cooling, the device may be optionally equipped with a temperature control element. In one aspect, the temperature control element is a thermoelectric element, such as a Peltier unit. A Peltier unit is a two-terminal bidirectional device capable of heating or cooling by reversing the direction of current flow through the Peltier element. Peltier elements are commercially available from Ferrotec (Bedford, N.H.). See also Muller, U.S. Pat. No. 5,830,208 and Bosniak. U.S. Pat. No. 5,169,358.

The Peltier element is preferably annular in shape and has an aperture extending therethrough from the first surface positioned in thermal communication with the patient's treatment site and the second surface. More particularly, thermal communication between the first surface of the Peltier element and the patient's treatment site may be achieved by providing the first surface in direct contact with the patient's treatment site or alternatively through indirect contact in a thermally conductive material, such as the therapeutic composition. While the aperture in the illustrative embodiments described below is substantially circular in shape, the shape of the aperture through the Peltier element can be readily varied in order to facilitate manufacture of the device and/or to optimize definition of the treatment area.

The Peltier element in the form of an annular ring is preferably mounted around the transducer edges or in various configurations across the transducer surface. Openings are provided in the Peltier element to allow the light ring. LEDs and/or lasers to transmit light and heat to the treatment area through the through the cap assembly.

In one mode of operation, a temperature sensor is coupled to the temperature control element. The temperature sensor can be any of several known devices, for example, a temperature resistance device, thermocouple, or other known temperature sensing device. The temperature sensor provides a feedback signal to the electrical control module operating the Peltier element. The temperature feedback signal is provided in any one of several ways. For example, the temperature feedback signal may be a temperature sensor that is mounted within the housing or on the patient's skin.

The temperature setpoint represents an expected temperature when the system is operating at a maximum rate. The Peltier heat/cool control circuit is operative to cause the Peltier element to selectively heat or cool the treatment site in response to the temperature sensor detecting a temperature that is respectively less than or greater than the temperature setpoint. Thus, for example, if the treatment site or device temperature is in excess of the desired temperature setpoint, the Peltier heat/cool control circuit causes the Peltier element to cool the device to the temperature setpoint. Alternatively, if the treatment site or device is at a temperature less than the temperature setpoint, the Peltier heat/cool control circuit operates the Peltier element to heat the treatment site or device back to the temperature setpoint. The temperature setpoint may be fixed, user selectable, or a constant value over time or even a value that varies as a function of some other parameter.

In order to augment the thermal treatment effects offered by the Peltier element and light source (e.g. the LEDs), a plurality of resistors may be positioned within the housing to transmit heal through the housing to elevate the treatment site temperature of a subject during the treatment process.

Therapeutic Agent

The device of the present invention is used to deliver a therapeutic agent to a treatment site on the skin. Thus, it is contemplated that the device could be used in conjunction with any topical agent. Such agents include but are not limited to antioxidants, growth factors, hormones, growth inhibitors, vitamins, exfoliators, skin toners (peptides), muscle relaxers (argireline), lubricants (glycerol), sunscreens, anti-wrinkling/anti-aging agents, antifungal agents, antibiotic agents, anti-acne and antipsoriatic agents, depigmentating agents, hydrators (hyaluronic acid, jojoba and olive oils and their extracts, phyto squalane), or muscle toners (especially substances that stimulate neurotransmitter activation, e.g., nerve growth factors), substances which provide a protective skin film (tritisol, phytopeptides, hydrolyzed wheat protein, marine elastin and algae and derivatives) or other substances that can be used to treat a patient's skin. Exemplary agents and formulations are set forth in Callaghan, U.S. Pat. No. 6,410,062; Dvoretzky et al., U.S. Published patent application No. 2005/0208115; McDaniel, U.S. Pat. No. 6,676,655; and Johnson et al., U.S. Pat. No. 5,947,921, which are incorporated by reference.

The preferred therapeutic agent for transdermal delivery is vitamin C. For the purposes of this patent application, the term "vitamin C" is intended to include ascorbic acid as well as its pharmaceutically acceptable salts and esters. Vitamin C is an antioxidant and acts as a scavenger or quencher of the free radicals. Thus, the presence of vitamin C thereby prevents oxidative tissue damage.

The amount of vitamin C present in the therapeutic compositions of the present invention is a therapeutically effective amount. A therapeutically effective amount of antioxidant is that amount of antioxidant necessary for the inventive composition to prevent and reduce injury to mammalian cells or increase the resuscitation rate of injured mammalian cells. The exact amount of antioxidant is a matter of preference subject to such factors as the type of condition being treated as well as the other ingredients in the composition. In a preferred aspect, the therapeutic composition comprises between about 2 and 35% wt % vitamin C, and most preferably between about and 10 to 25 wt % vitamin C. Typically, a therapeutic composition comprises about 200 to 800 milligrams of ascorbic acid or its pharmaceutically acceptable salts and esters.

As discussed above, the composition may also contain other therapeutic agents, such as collagen type I, vitamin A (retinol, palmitate), alpha-tocopherol (vitamin E), and particulate starch hydrolysate that are applied on wounds to promote the formation and growth of healthy granulation tissue. Preferably the therapeutic composition contains an antioxidant. In general, antioxidants arc substances which inhibit oxidation or suppress reactions promoted by oxygen or peroxides. Antioxidants, especially lipid-soluble antioxidants, can be absorbed into the cellular membrane to neutralize oxygen radicals and thereby protect the membrane. The antioxidants useful in the present invention are preferably selected from the group consisting of: all forms of tea or its extracts including, black, red, and green tea, all forms of vitamin A (retinol, palmitate), all forms of vitamin $A_2$(3,4-didehydroretinol), all forms of carotene such as alpha-carotene, beta-carotene, gamma-carotene, delta-carotene, all forms of vitamin C (D-ascorbic acid, L-ascorbic acid), all forms of tocopherol such as vitamin E (alpha-tocopherol, 3,4-dihydro-2,5,7,8-tetramethyl-2-(4,8,12-trimethyltri-decyl)-2H-1-benzopy ran-6-ol), beta-tocopherol, gamma-tocopherol, delta-tocopherol, tocoquinone, tocotrienol, and vitamin E esters which readily undergo hydrolysis to vitamin E such as vitamin E acetate and vitamin E succinate, and pharmaceutically acceptable vitamin E salts such as vitamin E phosphate, prodrugs of vitamin A, carotene, and vitamin E, pharmaceutically acceptable salts of vitamin A, carotene, and vitamin E, and the like, and mixtures thereof. Preferably, the additional antioxidant is selected from the group of lipid-soluble antioxidants consisting of vitamin A, beta-carotene, vitamin E, vitamin E acetate, and mixtures thereof. Dosing of each of these agents is well known to those skilled in the art, and can be readily determined using standard techniques.

The therapeutic composition generally comprises the therapeutic agent and a pharmaceutically acceptable carrier. The pharmaceutically acceptable carrier is preferably a liquid, cream, lotion, gel, or paste. The rheological properties of the carrier are such that the therapeutic composition can be readily dispensed from the device or applied manually to the treatment site. In one embodiment, the carrier system preferably comprises water. The carrier system in the second compartment may optionally comprise one or more organic solvents miscible with water. There are many mono, di, or polyhydric liquids suitable for this purpose including, for example, alcohols, glycols, and polyols. Without limitation, one or more of the following organic solvents may be employed ethanol, N-propanol, isopropyl alcohol, methanol, propylene glycol, butylene glycol, hexylene glycol, glycerine, sorbitol (polyol), di-propylene glycol, and polypropylene glycol. The organic solvent may comprise up to about 90% by weight of the carrier system. See generally Wilmott et al., U.S. Pat. No. 4,983,382, which is incorporated by reference. In addition, chelators or pH regulators, may be dissolved, dispersed, or emulsified in the carrier system. See generally Darr et al., U.S. Pat. No. 5,140,143, which is incorporated by reference.

In one aspect, the carrier includes a viscosity-modifying or gelling agent. Preferably, the viscosity of a therapeutic composition of this invention is at least 250,000 cps and most preferably at least 400,000 cps, or take the form a of a semi-solid gel. Examples of preferred viscosity modifying agents arc gelling agents which can be used in the present invention include guar gums, xanthan gums, propylene glycol, carrageenan, carboxymethylcellulose, cellulose, hydroxyalkyl celluloses (e.g., hydroxypropylmethylcellulose), sodium carboxycelluloses, Sepigel 305 (polyacrylamide/isoparaffin) and others sold by the company Seppic, polyurethanes, E-8/94 from the company Hoechst (polyacrylamidomethylpropanesulphonic acid), gelatin, agar, starch, etc.

In order to avoid obtaining a therapeutic composition which is too acidic (i.e., a pH less than 3.5) after introducing the ascorbic acid, it is preferable to add to the therapeutic composition one or more pH-regulating agents. Examples of such agents include sodium citrate or sodium acetate buffer. The quantity of buffer is a function of the quantity of ascorbic acid used and the desired final pH; the latter is typically from 3.0 to 6, more preferably from 3.8 to 4.5 but including all values and all ranges there between.

The prior art discloses several methods of incorporating vitamin C into cosmetic products for a variety of purposes, including the treatment of aging and photo-damaged skin, bleaching skin and regeneration of collagen. By way of example, Duraffourd et al., U.S. Pat. No. 4,668,516; Schinitsky, U.S. Pat. No. 4,938,969; and Parkinson, U.S. Pat. No. 4,518,614 disclose cosmetic compositions containing vitamin C. A composition for the regeneration of the collagen of connective skin tissue is disclosed in U.S. Pat. No. 4,668,516. The composition is for treating wrinkles by regenerating the collagen of the connective tissue of the skin by application of the solution to the skin. A composition for reducing wrinkle depth or intensity is disclosed in U.S. Pat. No. 4,938,969. The composition in an ointment or cream base contains ascorbic salt for topical application to the skin for the reduction of wrinkles therein. U.S. Pat. No. 4,518,614 relates to a composition containing ascorbic acid for moisturizing and softening skin for improving the texture thereof and diminishing superficial and deep wrinkles therein. Such patents are incorporated by reference.

In one aspect, the therapeutic composition forms part of a kit with the multi-modal device of the present invention. That is, the therapeutic composition is housed in a separate compartment or container, applied to the treatment site, and then transdermal delivery of the therapeutic composition is facilitated by applying the mechanical vibration energy, light energy, and thermal energy (heal/cooling) to the treatment site as desired. Preferred containers for vitamin C (and other therapeutic agents that are susceptible to oxidation) are set forth in Castel et al., U.S. patent application Ser. No. 12/195,788 for a Multiple-Compartment Applicator and Castel et al., U.S. patent application Ser. No. 12/049,800 for a Multi-Functional Applicator, which are both incorporated by reference.

In another aspect, the therapeutic composition is contained within the multi-modal device itself. In such a case, the device includes a reservoir containing a therapeutic agent for delivery to the treatment site. Typically, the therapeutic composition is expelled from the device by use of a suitable piston assembly. The piston head extends into the reservoir such that when the piston is actuated, the therapeutic composition in the reservoir is moved from the reservoir through one or more small conduits between the reservoir and the end of the device so that the therapeutic composition is delivered to the treatment site. The therapeutic composition may optionally be contained within a replaceable cartridge or pouch that is placed inside the reservoir. The reservoir conduit(s) and/or the cartridge opening(s) preferably contain frangible seals that are broken once the cartridge is installed and the piston is activated, thus allowing the therapeutic composition to move through the device to the transducer surface.

The device is especially useful in cosmetic applications, especially those following chemical peels, dermabrasion, ablative laser skin resurfacing, fractal laser resurfacing, RF and thermal resurfacing applications. The device can also be used through intact skin to reduce scarring, fine line wrinkles, and to rejuvenate the skin and underlying tissue. Typically, the device is used to apply antioxidants and other therapeutically useful agents efficiently through the skin while stimulating a biostimulative tissue repair response. It may be used daily or every few days for a typical 6-week course of treatment or following cosmetic procedures on a post-operative basis.

The following examples are illustrations of the present invention.

First Exemplary Embodiment

Figure 1A:
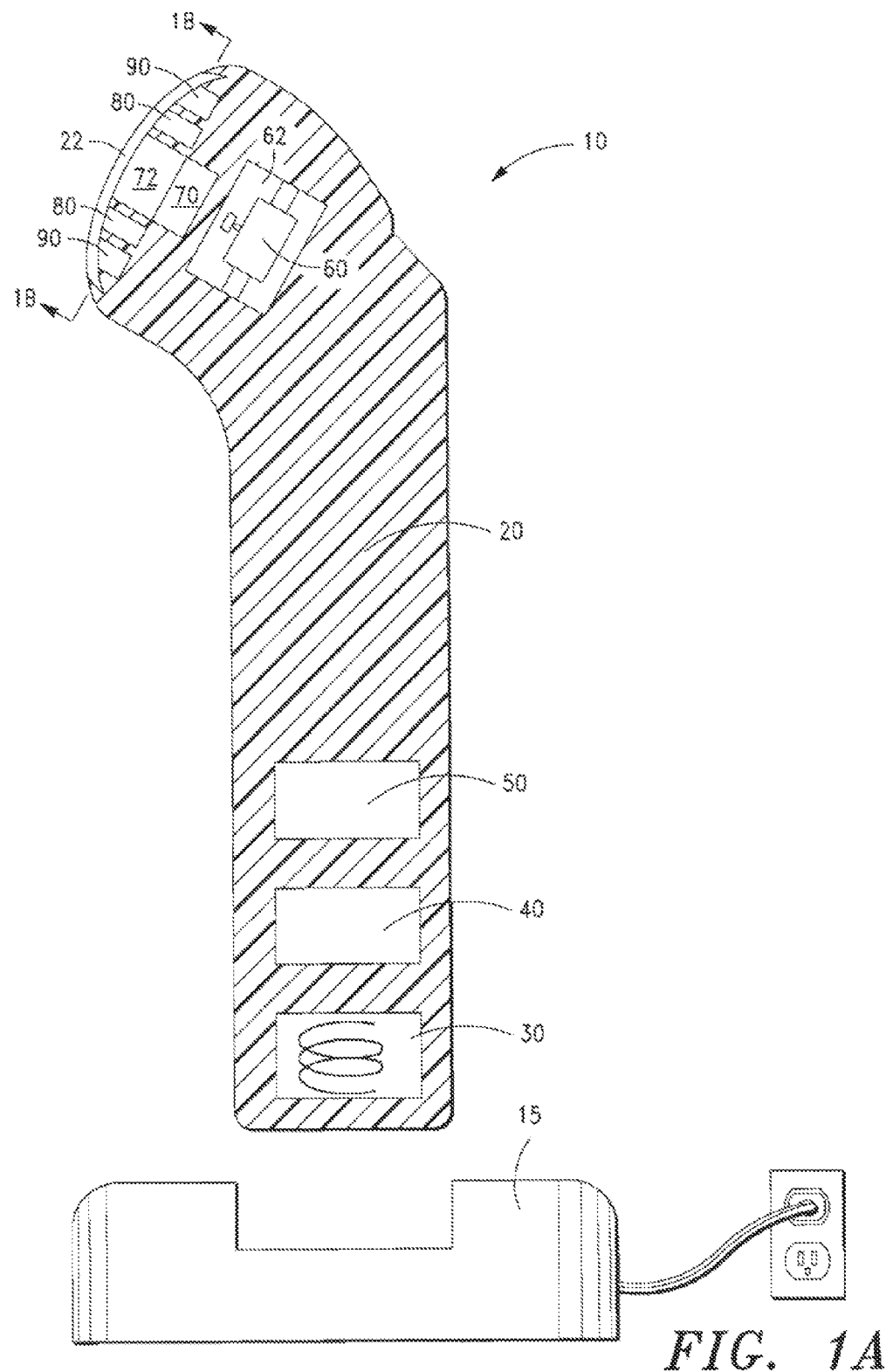
FIG. 1A illustrates cross-section of the multi-modal device shown in FIG. 1 taken through line 1A-1A.
Figure 1B:
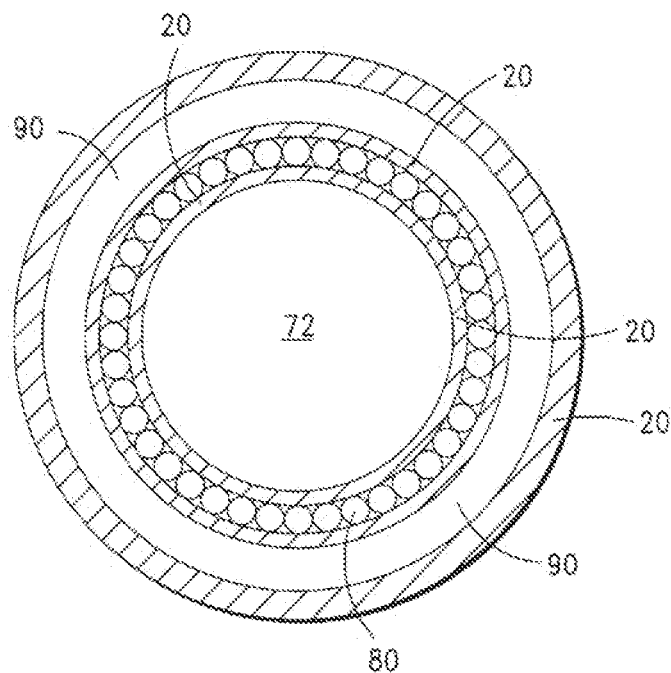
FIG. 1B illustrates cross-section of the multi-modal device shown in FIG. 1A taken through line 1B-1B.

FIGS. 1, 1A and 1B illustrate a device 10 in accordance with a first embodiment of the present invention. The inventive device 10 comprises a housing 20 for containing the mechanical vibration, light energy, and heating/cooling elements. For simplicity, the elements are shown in a block format. It will be appreciated to those skilled in the art that the device will be configured with the necessary wiring and circuits in order to permit the device to be operational as discussed herein.

As shown in FIG. 1 and FIG. 1A, the housing 20 is tubular or cylindrical in shape, and is comprised of injection-molded plastic. The housing is molded in so that the various components housed therein are positioned within cavities formed from the mold. A coil pick-up 30 together with an inductive battery charger 15, are used to charge the battery 50, which powers the electronic control module 40 and display panel 41 and other components in the device.

At one end of the device are the elements used to provide the desired treatment modality to a treatment site. The desired treatment modality is selected using the display panel 41. The housing has an internal cavity 62 for holding an electric buzzer 60. The buzzer is mounted on the housing so that vibrational energy from the buzzer is transmitted through the housing to the treatment site at a predetermined frequency or range of frequencies. An electronic control module 40 is used to control the the vibration frequency of the buzzer. Typically, the device is operated so that the vibrational frequency at the treatment site is between about 10 Hz and 1000 Hz modulated with about 15 kHz and 35 kHz harmonics. Alternatively, the buzzer could be operated at 15 kHz to 35 kHz and modulated with harmonics in the range of about 10 Hz to 1000 Hz, more preferably about 10 Hz to 100 Hz. An exemplary buzzer is available from Ningbo Tiyani Electronic Manufacture and Trade Company (Ningbo, China).

Above the buzzer 60 is an opening 72 in which a scanning laser 70 is positioned. The scanning laser 70 transmits light energy through the opening 72 and the cap assembly 22 to the treatment site. The electronic control module 40 is used to control the wavelength of the light energy, but typically the light applied to the treatment site is in the near-infrared range. The scanning laser is configured to transmit a continuous beam of light energy toward the treatment site. Alternatively, the electronic control module 40 may control the frequency at which the laser and/or the LEDs pulses the light energy. Typically, the device is operated so that pulsing frequency of the light energy from the laser 70 is synchronized with the vibrational frequency from the buzzer 60 at the treatment site. That is, the vibrational frequency of the buzzer and the pulsing frequency of the near-infrared light are preferably synchronized between about 15 kHz and 35 kHz.

One or more LEDs 80 are positioned adjacent to the opening 72 and the laser 70. The LEDs 80 are preferably positioned in an annular manner as shown in FIG. 1A and FIG. 1B. The electronic control module 40 is used to control the wavelength of the light energy from the LEDs by activating different LEDs in the assembly, but typically the light is in the near-infrared range. The wavelength of the light generated by the LEDs may be the same or different than the wavelength of the light transmitted by the laser. The LEDs may transmit a continuous beam of light energy toward the treatment site.

Alternatively, the electronic control module 40 may control the frequency at which the laser pulses the light energy. Typically, the device is operated so that pulsing frequency of the light near-infrared energy is synchronized with the vibrational frequency from the buzzer at the treatment site. That is, the vibrational frequency of the buzzer and the pulsing frequency of the near-infrared light (either or both of the LEDs and the laser) are preferably synchronized and between about 15 kHz and 35 kHz.

As shown in FIG. 1A, a Peltier element 90 is positioned adjacent to the LEDs. The Peltier element is preferably annular in shape as generally shown in FIG. 1B. The Peltier element is positioned in thermal communication with the patient's skin. Although FIG. 1A illustrates that the cap assembly 22 overlies the Peltier element, the Peltier element can be positioned so that it is in direct contact with the patient's skin or alternatively through indirect contact via a thermally conductive material.

Second Exemplary Embodiment

Figure 2A:
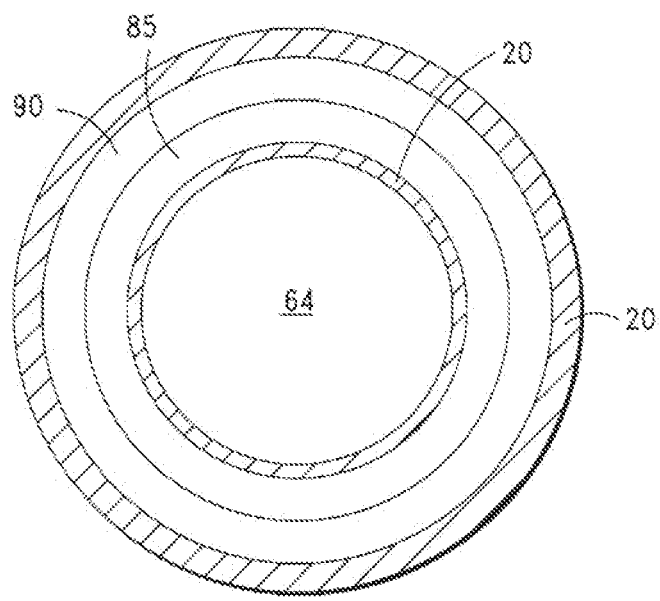
FIG. 2A illustrates cross-section of the multi-modal device shown in FIG. 2 taken through line 2A-2A.
Figure 2:
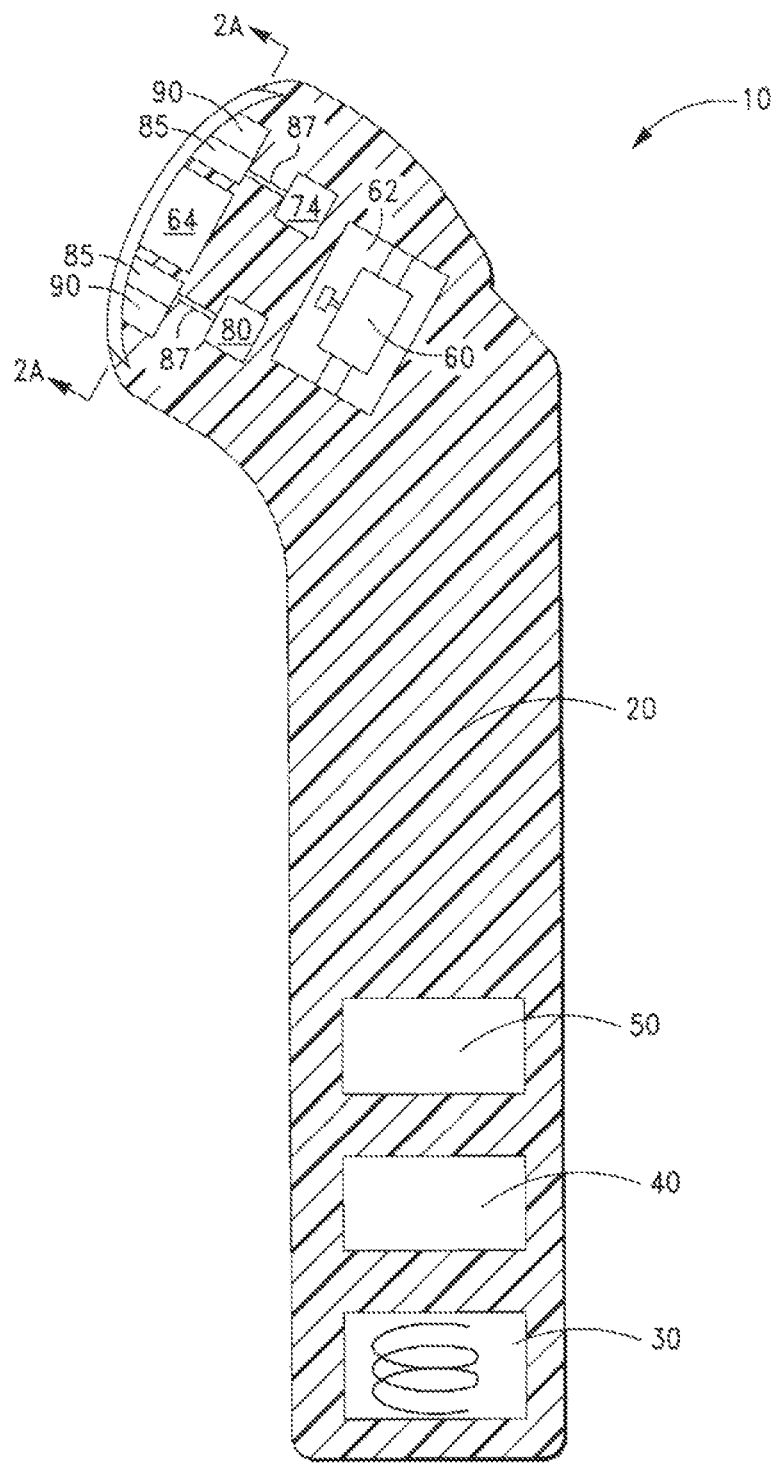
FIG. 2 illustrates a cross-section of a multi-modal device for the delivery of a topical therapeutic agent in accordance with a second embodiment of the present invention.

FIGS. 2 and 2A illustrate a device 10 in accordance with a second embodiment of the present invention. The second embodiment is similar to the first embodiment except that the light energy from either the LEDs or the lasers is transmitted through a light pipe or light ring. Further, in the second embodiment, an ultrasonic transducer is used to generate the vibrational energy.

As with the first embodiment, the inventive device 10 comprises a housing 20 for containing the mechanical vibration, light energy, and optional heating/cooling elements. In this embodiment, an ultrasonic transducer 64 is used to deliver vibrational energy to the treatment site at a predetermined frequency. The electronic control module 40 is used to control the frequency of the transducer. Typically, the device is operated so that the vibrational frequency at the treatment site is between about 15 kHz and 35 kHz. As another example, the device is operated so that the vibrational frequency at the treatment site is between about 100 kHz and 5 MHz modulated with harmonics of between about 15 kHz and 35 kHz. An exemplary ultrasonic transducer is commercially available as PZT Material from Staveley Sensors, Ltd (Hartford, Conn.). An optional buzzer or low frequency vibrational element may also be provided. The housing has an internal cavity 62 for holding an electric buzzer 60. The buzzer is mounted on the housing so that vibrational energy from the buzzer is transmitted through the housing to the treatment site at a predetermined frequency or range of frequencies. An electronic control module 40 is used to control the the vibration frequency of the buzzer. Typically, the device is operated so that the vibrational frequency at the treatment site is between about 10 Hz to 1000 Hz, more preferably about 10 Hz to 100 Hz.

An annular light pipe or light ring 85 is positioned around the ultrasonic transducer 64. Light from one or more LEDs 80 and/or non-scanning lasers 74 is transmitted through one or more optical fibers 87 to the light pipe 85. The light pipe operates as a luminance, generating an annular pattern (or other preferred pattern based on the configuration of the light pipe) of light against the treatment site. The leakage of the light from the light pipe is preferably controlled so that substantially all (preferably more than 50%, 60%, 70%, 80%, or 90%) of the light is transmitted towards the treatment site.

The electronic control module 40 is used to control the wavelength of the light energy (whether from the LEDs, or the non-scanning laser 74, or a combination thereof), but typically the light applied to the treatment site is in the near-infrared range. It will be appreciated that the light generated by the LEDs and laser may have the same or different wavelengths. The light pipe may thus transmit a continuous beam of light energy toward the treatment site. Alternatively, the electronic control module 40 may control the frequency at which the LEDs 80 and/or laser 74 pulse the light energy. Typically, the device is operated so that the pulsing frequency of the light near-infrared energy is synchronized with the vibrational frequency from the ultrasonic transducer 64 at the treatment site. That is, the vibrational frequency of the ultrasonic transducer and the pulsing frequency of the near-infrared light are preferably synchronized and between about 15 kHz and 35 kHz.

As shown in FIG. 2, an optional Peltier element 90 is positioned adjacent to the light pipe 85. The Peltier element is preferably annular in shape as generally shown in FIG. 2A. The Peltier element is positioned in thermal communication with the patient's skin. Although FIG. 2 illustrates that a cap assembly overlies the Peltier element, the Peltier element can be positioned so that it is in direct contact with the patient's skin or alternatively through indirect contact via a thermally conductive material.

Third Exemplary Embodiment

Figure 3:
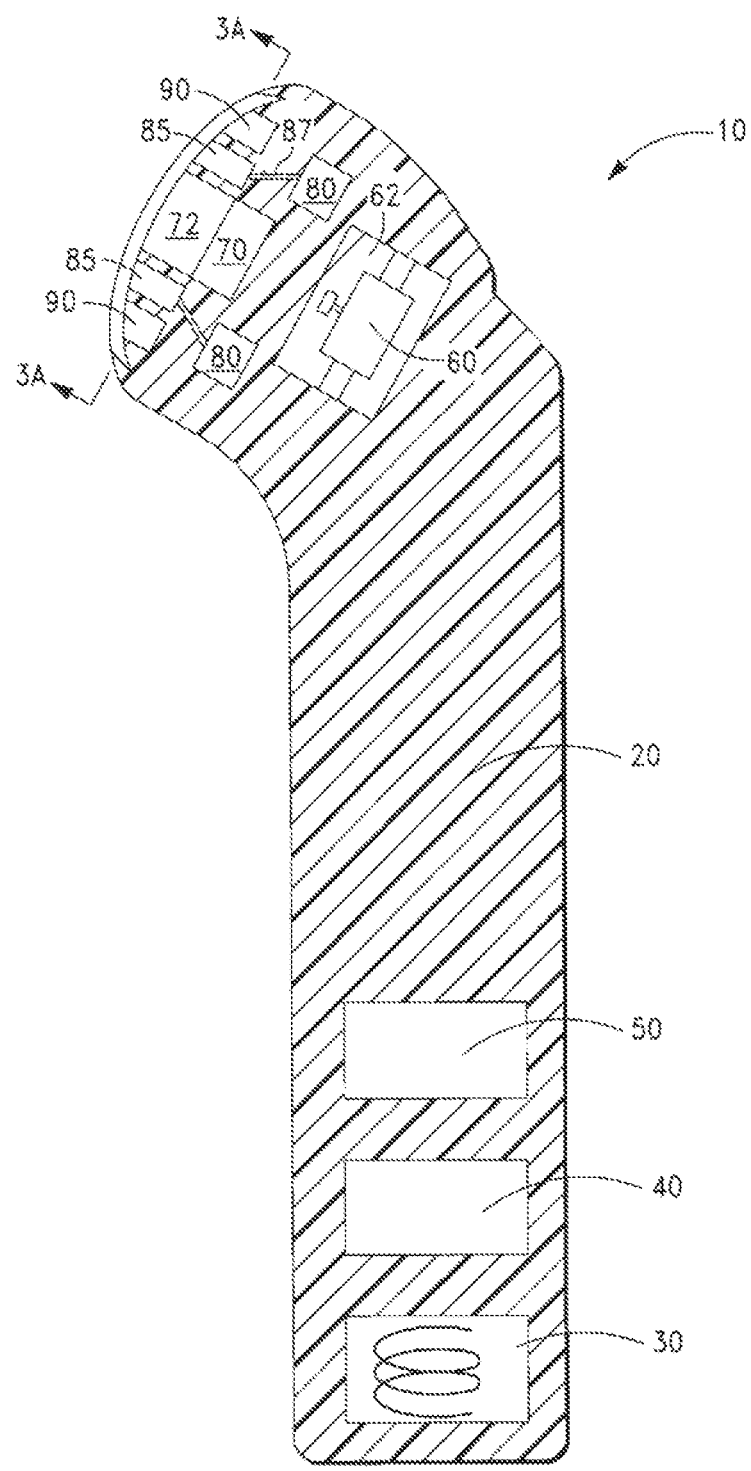
FIG. 3 illustrates a cross-section of a multi-modal device for the delivery of a topical therapeutic agent in accordance with a third embodiment of the present invention.
Figure 3A:
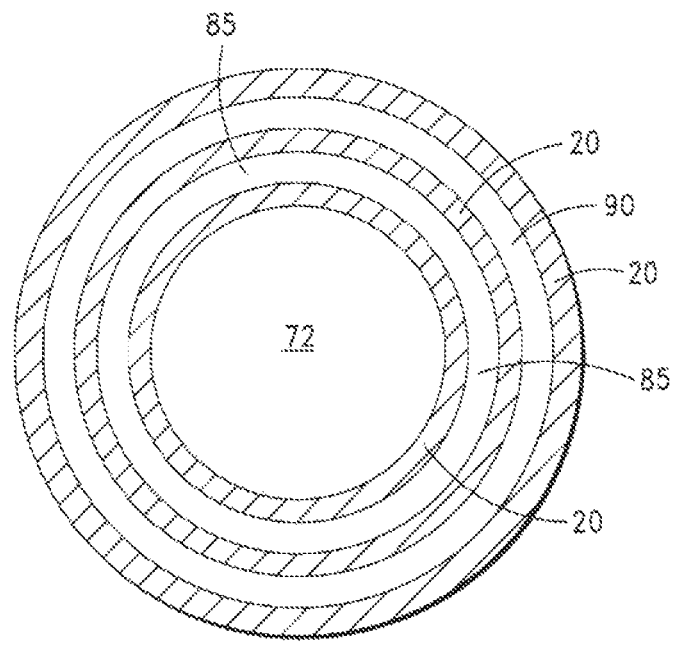
FIG. 3A illustrates cross-section of the multi-modal device shown in FIG. 3 taken through line 3A-3A.

FIGS. 3 and 3A illustrate a device 10 in accordance with a third embodiment of the present invention. The third embodiment is similar to the second embodiment except that the light energy from the LEDs only is transmitted through a light pipe or light ring. Further, in the third embodiment, a scanning laser 70 is also used to deliver light to treatment site, and a buzzer 60 is used to generate the vibrational energy.

The inventive device 10 comprises a housing 20 for containing the mechanical vibration, light energy, and heating/cooling elements. The housing has an internal cavity 62 for holding an electric buzzer 60. The buzzer is mounted on the housing so that vibrational energy from the buzzer is transmitted through the housing to the treatment site at a predetermined frequency. The electronic control module 40 is used to control the frequency of the buzzer. Typically, the device is operated so that the vibrational frequency at the treatment site between about 10 Hz and 1000 Hz modulated with harmonics between about 15 kHz and 35 kHz.

Above the module 60 is an opening 72 in which a scanning laser 70 is positioned. The scanning laser 70 transmits light energy through the opening 72 and the cap assembly 22 to the treatment site. The electronic control module 40 is used to control the wavelength of the light energy, but typically the light applied to the treatment site is in the near-infrared range. The scanning laser is configured to transmit a continuous beam of light energy toward the treatment site. Alternatively, the electronic control module 40 may control the frequency at which the laser pulses the light energy. Typically, the device is operated so that the pulsing frequency of the light near-infrared energy is synchronized with the vibrational frequency from the buzzer at the treatment site. That is, the vibrational frequency of the buzzer and the pulsing frequency of the near-infrared light are preferably synchronized and between about 15 kHz and 35 kHz.

An annular light pipe or light ring 85 is positioned at the end of the device. Light from one or more LEDs 80 is transmitted through one or more optical fibers 87 to the light pipe 85. The light pipe operates as a luminare, generating an annular pattern (or other preferred pattern, such as an oval or clover) of light against the treatment site. The leakage of the light from the light pipe is preferably controlled so that substantially all (preferably more than 50%, 60%, 70%, 80%, or 90%) of the light is transmitted towards the treatment site.

The electronic control module 40 is used to control the wavelength of the light energy (whether from the LEDs, or the scanning laser 70, or a combination thereof), but typically the light applied to the treatment site is in the near-infrared range. The light pipe may thus transmit a continuous beam of light energy toward the treatment site. Alternatively, the electronic control module 40 may control the frequency at which the LEDs 80 and/or laser 72 pulses the light energy. Typically, the device is operated so that pulsing frequency of the light near-infrared energy is synchronized with the vibrational frequency from the buzzer 60 at the treatment site. That is, the vibrational frequency of the buzzer and the pulsing frequency of the near-infrared light are preferably synchronized and between about 15 kHz and 35 kHz.

As shown in FIG. 3, a Peltier clement 90 is positioned adjacent to the light pipe 85. The Peltier element is preferably annular in shape as generally shown in FIG. 3A. The Peltier element is positioned in thermal communication with the patient's skin. Although FIG. 3 illustrates that a cap assembly overlies the Peltier clement, the Peltier clement can be positioned so that it is in direct contact with the patient's skin or alternatively through indirect contact thermally conductive material.

Fourth Exemplary Embodiment

Figure 4A:
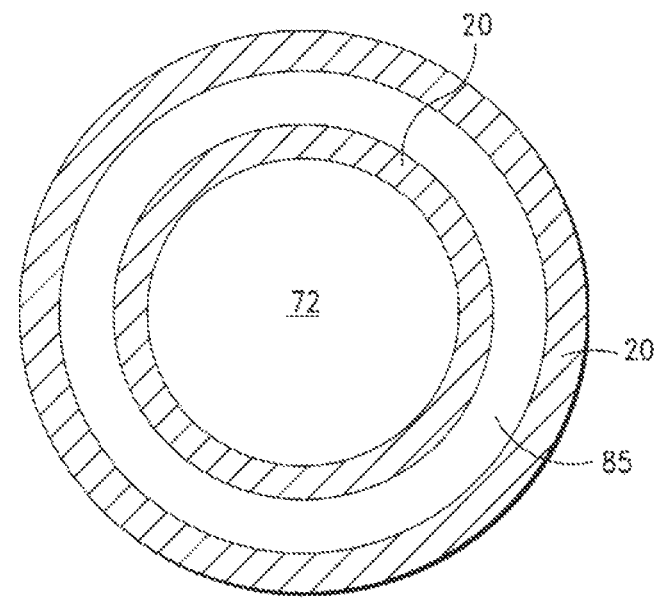
FIG. 4A illustrates cross-section of the multi-modal device shown in FIG. 4 taken through line 4A-4A.
Figure 4:
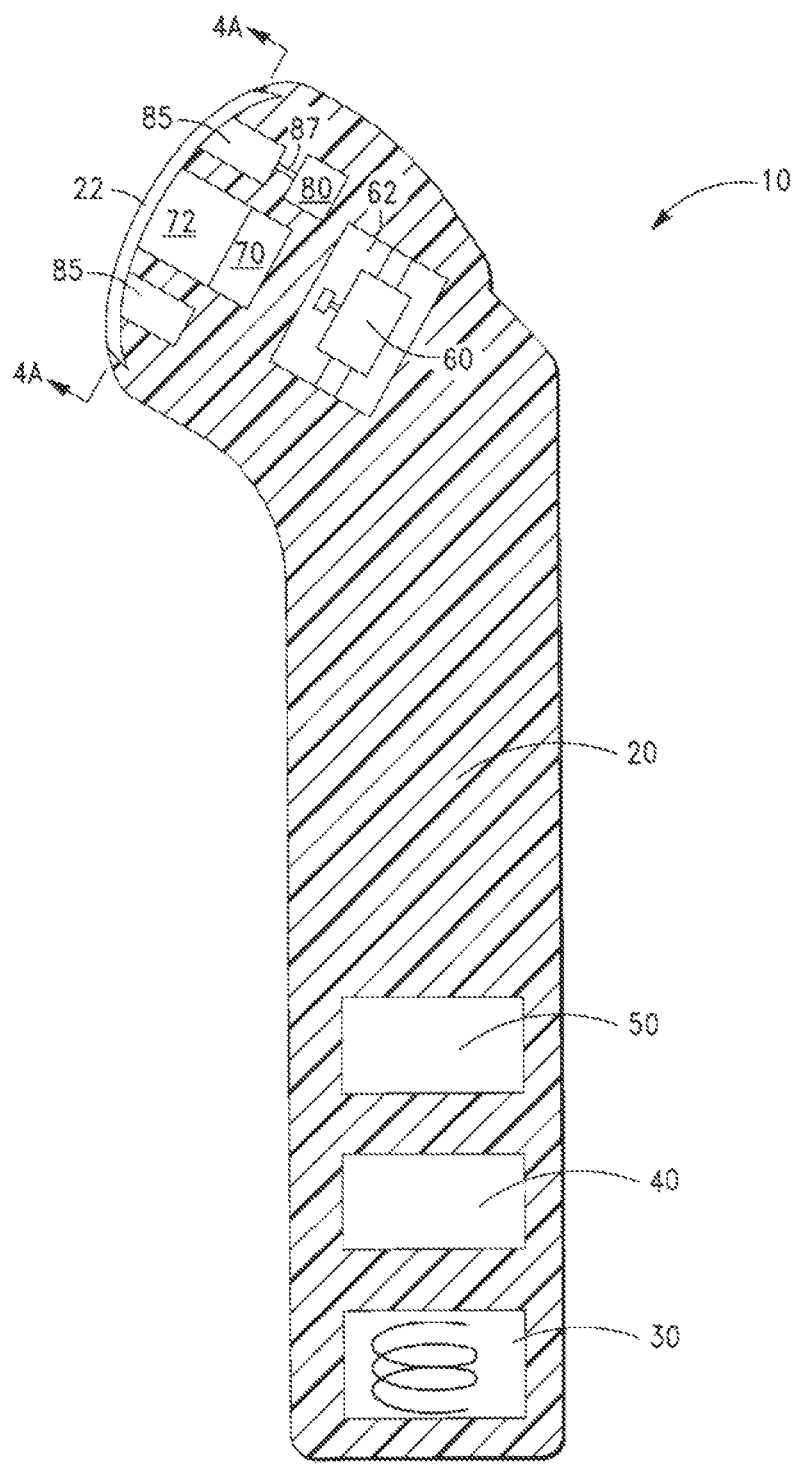
FIG. 4 illustrates a cross-section of a multi-modal device for the delivery of a topical therapeutic agent in accordance with a fourth embodiment of the present invention.

FIGS. 4 and 4A illustrate a device 10 in accordance with a fourth embodiment of the present invention. The fourth embodiment is similar to the First embodiment except that the device does not contain a Peltier clement.

The inventive device 10 comprises a housing 20 for containing the mechanical vibrational and light energy elements. The housing has an internal cavity 62 for holding an electric buzzer 60. The buzzer is mounted on the housing so that vibrational energy from the buzzer is transmitted through the housing to the treatment site at a predetermined frequency. The electronic control module 40 is used to control the frequency of the buzzer. Typically, the device is operated so that the vibrational frequency at the treatment site between about 10 Hz and 1000 Hz modulated with about 15 kHz and 35 kHz harmonics.

Above the buzzer 60 is an opening 72 in which a scanning laser 70 is positioned. The scanning laser 70 transmits light energy through the opening 72 and the cap assembly 22 to the treatment site. The electronic control module 40 is used to control the wavelength of the light energy, but typically the light applied to the treatment site is in the near-infrared range. The scanning laser is configured to transmit a continuous beam of light energy toward the treatment site. Alternatively, the electronic control module 40 may control the frequency at which the laser pulses the light energy. Typically, the device is operated so that pulsing frequency of the light near-infrared energy is synchronized with the vibrational frequency from the buzzer at the treatment site. That is, the vibrational frequency of the buzzer and the pulsing frequency of the near-infrared light are preferably synchronized and between about 15 kHz and 35 kHz.

An annular light pipe or light ring 85 is positioned at the end of the device. Light from one or more LEDs 80 is transmitted through one or more optical fibers 87 to the light pipe 85. The light pipe operates as a luminare, generating an annular pattern (or other preferred pattern) of light against the treatment site. The leakage of the light from the light pipe is preferably controlled so that substantially all (preferably more than 50%, 60%, 70%, 80%, or 90%) of the light is transmitted towards the treatment site.

The electronic control module 40 is used to control the wavelength of the light energy (whether from the LEDs, or the scanning laser 70, or a combination thereof), but typically the light applied to the treatment site is in the near-infrared range. The light pipe may thus transmit a continuous beam of light energy toward the treatment site. Alternatively, the electronic control module 40 may control the frequency at which the LEDs 80 and/or laser 72 pulses the light energy. Typically, the device is operated so that pulsing frequency of the light near-infrared energy is synchronized with the vibrational frequency from the buzzer 60 at the treatment site. That is, the vibrational frequency of the buzzer and the pulsing frequency of the near-infrared light are preferably synchronized and between about 15 kHz and 35 kHz.

Fifth Exemplary Embodiment

Figure 5:
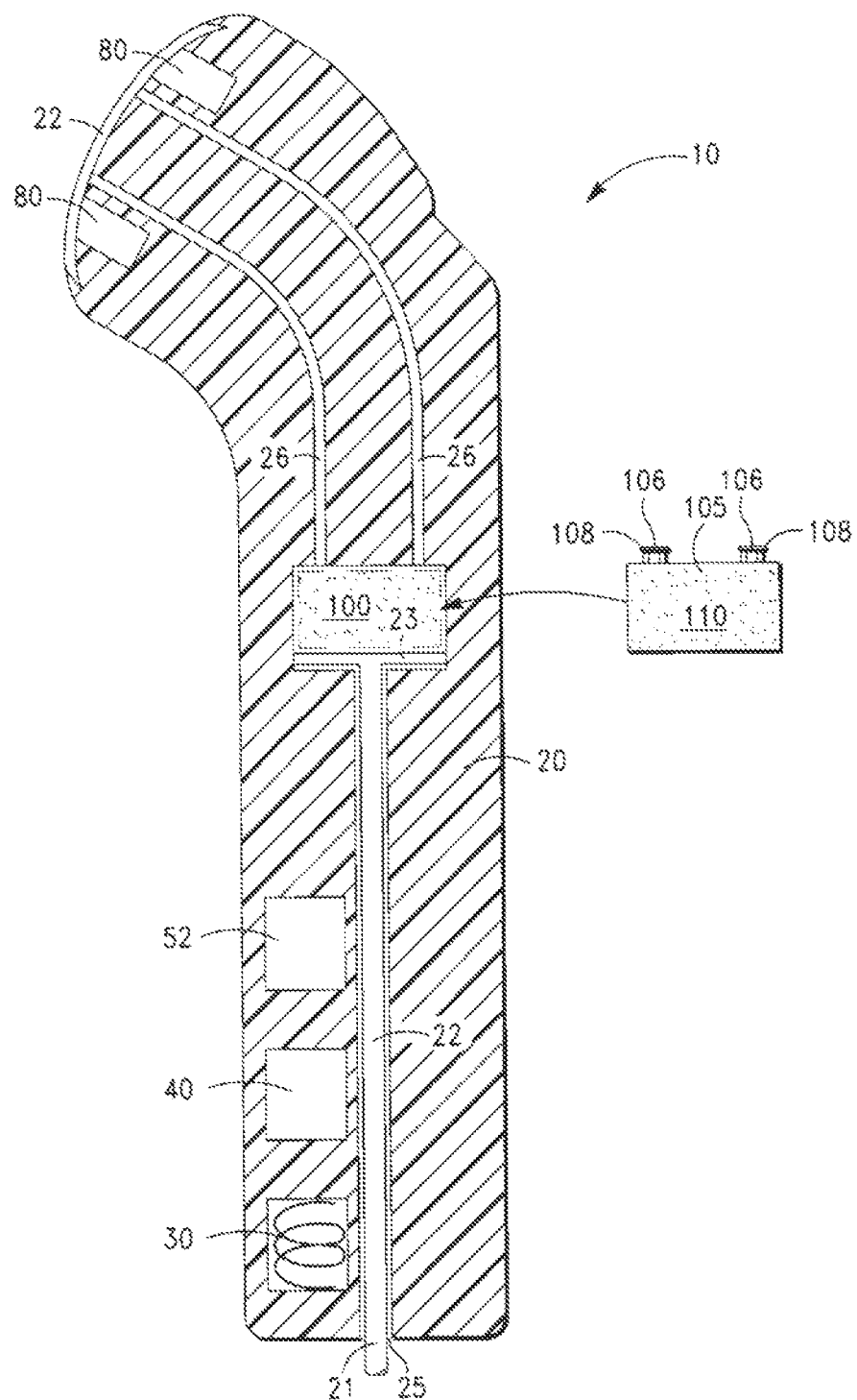
FIG. 5 illustrates a cross-section of a multi-modal device for the delivery of a topical therapeutic agent in accordance with a fifth embodiment of the present invention.
Figure 5A:
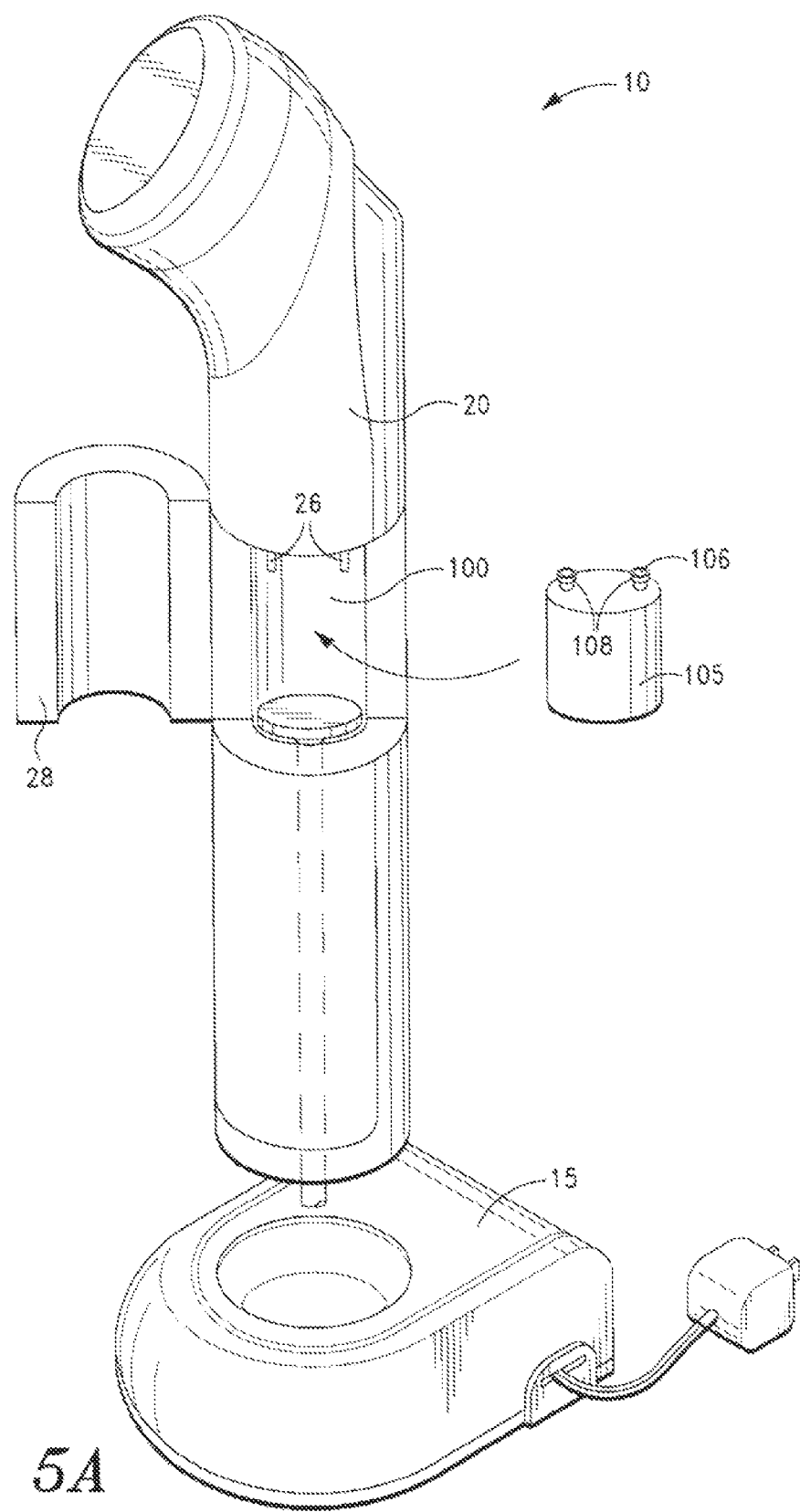
FIG. 5A is a perspective view of the multi-modal device shown in FIG. 5, illustrating the removable reservoir.

FIGS. 5 and 5A illustrate a device 10 in accordance with a fifth embodiment of the present invention. The device includes a reservoir 100 containing a therapeutic agent 110 for delivery to the treatment site.

In this embodiment, the housing includes an elongated opening 25, in which the shaft 22 of a piston 21 is positioned. The piston head 23 extends into the reservoir 110 such that when the piston 21 is actuated, the therapeutic agent 110 in the reservoir is moved from the reservoir through one or more small conduits 26 to the treatment site.

In this embodiment a replaceable cartridge or pouch 105 shown on FIG. 5A is placed within the reservoir 100 for dispensing the therapeutic agent. The cartridge or pouch is flexible but contains openings 106 covered with frangible seals 108 which are aligned with the conduits 26 in the housing. As the piston is actuated, the piston head 23 applies pressure to the flexible cartridge or pouch, thereby breaking the frangible seals 108 and moving the therapeutic agent from the reservoir to the conduits. The flexible cartridge or pouch 105 may be accessed and replaced by the user using an access door 28.

One or more LEDs 80 or lasers are positioned adjacent to the conduit 26 exit. The LEDs 80 arc preferably positioned in an annular manner as previously described herein (e.g., in FIG. 1A). The electronic control module 40 is used to control the wavelength of the light energy from the LEDs, but typically the light is in the near-infrared range. Alternatively, the electronic control module 40 may control the frequency at which the laser pulses the light energy. A disposable or rechargeable battery 52 is used to power the device. A coil pick-up 30 together with an inductive battery charger are used to charge the battery 52, which powers the electronic control module 40.

Although not illustrated in FIG. 5, a mechanical vibration element, such as the buzzer 60 shown in FIG. 1 or an ultrasonic transducer as shown in FIG. 2, can be optionally incorporated into the device. Further, a magnetic vibrator or voice coil may be optionally incorporated into the device. Lastly a Peltier element can be optionally incorporated into the device. The Peltier element is preferably annular in shape as generally shown in FIG. 1A. The Peltier clement is positioned in thermal communication with the patient's skin. Although FIG. 1A illustrates that a cap assembly overlies the Peltier element, the Peltier element can be positioned so that it is in direct contact with the patient's skin or alternatively through indirect contact thermally conductive material.

Sixth Exemplary Embodiment

Figure 6:
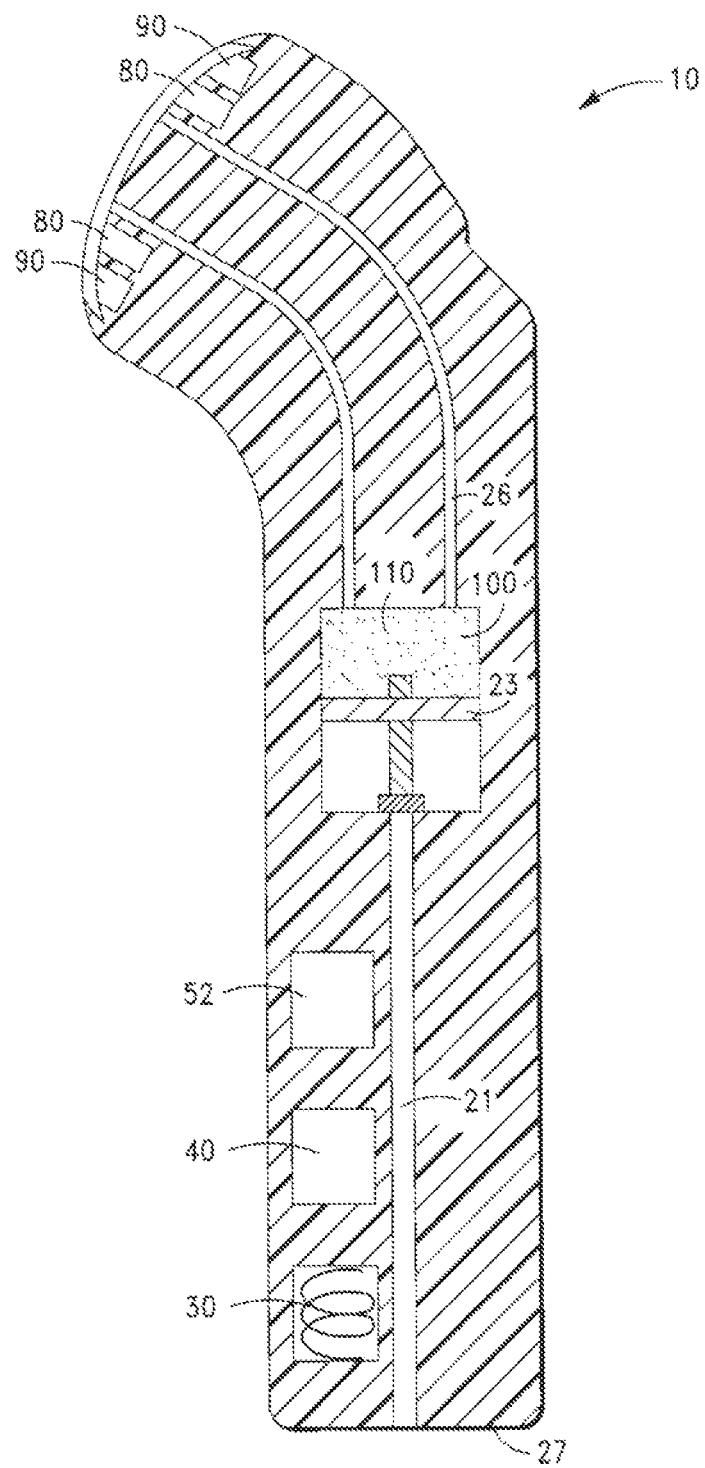
FIG. 6 illustrates a cross-section of a multi-modal device for the delivery of a topical therapeutic agent in accordance with a fifth embodiment of the present invention.

FIG. 6 illustrates a device 10 in accordance with a sixth embodiment of the present invention. The device includes a reservoir 100 containing a therapeutic agent 110 for delivery to the treatment site. This embodiment is similar to the fifth embodiment except that an annular Peltier element 90 is further included in the device. In addition, the therapeutic agent 110 is housed inside the reservoir 100, but the device docs not contain a removable cartridge or pouch. Further, the device is powered substantially as set forth in the first embodiment. Lastly, the device contains an alternative dispenser for the therapeutic agent 110.

In this embodiment, the housing includes a piston assembly as generally outlined in U.S. Pat. No. 2,442,503, which is incorporated by reference. The piston head 23 extends into the reservoir 100 such that when the piston 21 is actuated using knob 27, the therapeutic agent 110 in the reservoir is moved from the reservoir through one or more small conduits 26 to the treatment site.

One or more LEDs 80 or lasers are positioned adjacent to conduit 26 exit. The LEDs 80 or lasers are preferably positioned in an annular manner as previously shown in FIG. 1A. The electronic control module 40 is used to control the wavelength of the light energy from the LEDs, or lasers, but typically the light is in the near-infrared range. Alternatively, the electronic control module 40 may control the frequency at which the laser pulses the light energy.

As shown in FIG. 6, a Peltier element 90 is position adjacent to the LEDs or lasers. The Peltier element is preferably annular in shape as generally shown in FIG. 1A. The Peltier element is positioned in thermal communication with the patient's skin. Although FIG. 6 illustrates that a cap assembly overlies the Peltier element, the Peltier element can be positioned so that it is in direct contact with the patient's skin or alternatively through indirect contact thermally conductive material.

Although not illustrated in FIG. 6, a mechanical vibration element, such as the buzzer 60 shown in FIG. 1 or an ultrasonic transducer as shown in FIG. 2 can be optionally incorporated into the device. Further, a magnetic vibrator or voice coil may be optionally incorporated into the device.

From the foregoing, it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth or shown in the accompanying drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A device for the transdermal delivery of a therapeutic agent to the skin at a treatment site comprising a housing containing:
    a mechanical vibration element, wherein said mechanical vibration element is selected from the group consisting of (a) a mechanical vibration element which produces mechanical energy having a frequency of about 15 kHz to 100 kHz; (b) a mechanical vibration element which produces mechanical energy having a frequency of about 100 kHz to 5 MHz modulated with mechanical energy having a frequency of about 15 kHz to 100 kHz; and (c) a mechanical vibration element which produces mechanical energy having a frequency of about 10 Hz to 1000 Hz modulated with mechanical energy having a frequency of about 15 kHz to 100 kHz;
    a light source;
    a heating and/or cooling element;
    a power source for powering said mechanical vibrational element, light source, and heating and/or cooling element; and
    an electronic control module for controlling said mechanical vibrational element, light source, and heating and/or cooling element.

2. The device of claim 1 wherein said mechanical vibrational element, light source, and heating and/or cooling element are positioned within an injection molded housing.

3. The device of claim 2 further comprising a reservoir in said housing, said reservoir having a therapeutic composition therein.

4. The device of claim 3 further wherein said therapeutic composition comprises a therapeutically effective amount of ascorbic acid or its pharmaceutically acceptable salts and esters.

5. The device of claim 1 wherein said mechanical vibration element comprises an ultrasonic transducer having an operating frequency of between about 15 kHz and 35 kHz.

6. The device of claim 1 wherein said mechanical vibration element produces mechanical energy having a frequency of about 100 kHz to 5 MHz modulated with mechanical energy having a frequency of about 15 kHz to 100 kHz.

7. The device of claim 6 wherein said light source produces light having a wavelength between about 600 nm and 1650 nm and modulated with a light modulation frequency that is synchronized with said mechanical energy modulation frequency.

8. The device of claim 1 wherein said mechanical vibration element produces mechanical energy having a frequency of about 10 Hz to 1000 Hz modulated with mechanical energy having a frequency of about 15 kHz to 100 kHz.

9. The device of claim 8 wherein said light source produces light having a wavelength between about 600 nm and 1650 nm and modulated with a light modulation frequency that is synchronized with said mechanical energy modulation frequency.

10. The device of claim 6 wherein said mechanical vibration element provides said modulation at a first modulation frequency for a first period of time followed by a second modulation frequency for a second period of time.

11. The device of claim 10 where said mechanical vibration element provides said modulation at a third modulation frequency for a third period of time.

12. The device of claim 8 wherein said mechanical vibration element provides said modulation at a first modulation frequency for a first period of time followed by a second modulation frequency for a second period of time.

13. The device of claim 12 where said mechanical vibration element provides said modulation at a third modulation frequency for a third period of time.

14. The device of claim 6 wherein light source is modulated synchronously with the mechanical vibration element, and said modulation is at a first modulation frequency for a first period of time followed by a second modulation frequency for a second period of time.

15. The device of claim 14 where said mechanical vibration element and said light source provides said modulation at a third modulation frequency for a third period of time.

16. The device of claim 1 wherein said mechanical vibration element comprises an ultrasonic transducer which produces ultrasound having a frequency of about 100 kHz to 5 MHz modulated with an ultrasonic frequency of about 15 kHz and 100 kHz.

17. The device of claim 16 wherein said light source produces light having a wavelength between about 600 nm and 1650 nm and modulated with a light modulation frequency that is synchronized with said ultrasonic modulation frequency.

18. The device of claim 1 wherein said mechanical vibration element is selected from the group consisting of an ultrasonic transducer, motor having an offset cam, buzzer, voice coil, and magnetic transducer.

19. The device of claim 1 wherein said light source comprises a plurality of light emitting diodes or lasers having a wavelength between about 600 and 1650 nm.

20. The device of claim 1 wherein said heating and/or cooling element comprises a Peltier element.

21. The device of claim 1 wherein said mechanical vibration element comprises an ultrasonic transducer having a frequency between about 15 kHz and 100 kHz, said light source comprises a plurality of light emitting diodes having a wavelength between about 600 nm and 1650 nm, and said heating and/or cooling element comprises a Peltier element, and further comprising a reservoir in said housing, and reservoir having a therapeutic composition comprising about 2 wt % to 35 wt % ascorbic acid or its pharmaceutically acceptable salts and esters.

22. The device of claim 21 further comprising a piston having a piston head positioned in said reservoir and adapted to dispense said therapeutic composition from said housing.

23. The device of claim 21 wherein said therapeutic composition is contained in a replaceable cartridge or pouch in said reservoir.

24. The device of claim 23 wherein said replaceable cartridge or pouch has a frangible seal.

25. The device of claim 1 wherein said a mechanical vibration element comprises an ultrasonic transducer and said light source comprises a light ring, said light ring being positioned annularly around said ultrasonic transducer.

26. The device of claim 1 wherein said mechanical vibration element comprises an ultrasonic transducer and said heating and/or cooling element comprises a Peltier element, wherein said Peltier element is positioned annularly around said ultrasonic transducer.

27. The device of claim 1 wherein said light source comprises a laser having a wavelength between about 600 nm and 1650 nm which generates light energy pulsed at laser modulation frequency between about 15 kHz and 100 kHz.

28. The device of claim 27 wherein said light source further comprises a light emitting diode, and light energy generated by said light emitting diode is superimposed with said light energy from said laser.

29. The device of claim 1 wherein said housing has a patterned etched cap assembly for allowing light from said light source to be applied to said treatment site in a predetermined pattern.

30. The device of claim 1 further comprising an audible or visual alert for alerting a user that a treatment time has been met.

31. A kit comprising the device of claim 1 and a container having a therapeutic composition housed therein.

32. A method for transdermally delivering a therapeutic agent to a patient's treatment site on the skin comprising:
(a) decreasing the temperature of the treatment site by cooling the treatment site;
(b) applying mechanical energy the treatment site, said mechanical energy having a frequency selected from the group consisting of (i) a frequency of about 15 kHz to 100 kHz; (ii) a frequency of about 100 kHz to 5 MHz modulated with mechanical energy having a frequency of about 15 kHz to 100 kHz; and (iii) a frequency of about 10 Hz to 1000 Hz modulated with mechanical energy having a frequency of about 15 kHz to 100 kHz;
(c) applying light energy to said treatment site; and
(d) applying a composition comprising a therapeutically effective amount of said therapeutic agent.

33. The method of claim 32 wherein steps (a), (b), (c), and (d) are performed simultaneously.

34. The method of claim 32 wherein said applying mechanical energy step comprises applying mechanical energy having a frequency of about 100 kHz to 5 MHz modulated with mechanical energy having a frequency of about 15 kHz and 100 kHz.

35. The method of claim 34 wherein said applying light energy step comprises applying light having a wavelength between about 600 nm and 1650 nm and modulated with a light modulation frequency that is synchronized with said mechanical energy modulation frequency.

36. The method of claim 32 wherein said applying mechanical energy step comprises applying said mechanical energy at a first modulation frequency for a first period of time followed by a second modulation frequency for a second period of time.

37. The method of claim 32 wherein said light energy is modulated synchronously with said mechanical energy and said modulation is at a first modulation frequency for a first period of time followed by a second modulation frequency for a second period of time.

38. The method of claim 37 wherein said light energy and said mechanical energy are modulated at a third modulation frequency for a third period of time.

39. The method of claim 32 wherein said applying mechanical energy step comprises applying mechanical energy having a frequency of about 10 Hz to 1000 Hz modulated with a mechanical energy having a frequency of about 15 kHz to 100 kHz.

40. The method of claim 39 wherein said applying light energy step comprises applying light having a wavelength between about 600 nm and 1650 nm and modulated with a light modulation frequency that is synchronized with said mechanical energy modulation frequency.

41. The method of claim 32 wherein said applying mechanical energy step comprises applying ultrasound having a frequency of about 100 kHz to 5 MHz modulated with a ultrasonic modulation frequency of about 15 kHz to 100 kHz.

42. The method of claim 41 wherein said applying light energy step comprises applying light having a wavelength between about 600 nm and 1650 nm and modulated with a light modulation frequency that is synchronized with said ultrasonic modulation frequency.

43. The method of claim 32 where said light energy is provided by a light emitting diode or scanning laser.

44. The method claim 32 wherein said light energy has a wavelength between 600 nm and 650 nm and an energy density of about 1 to 20 J/cm$^2$.

45. The method of claim 32 wherein said mechanical energy is provided by an ultrasonic transducer, motor having an offset cam, voice coil, buzzer, or magnetic transducer.

46. The method of claim 32 wherein said therapeutic agent is ascorbic acid or its pharmaceutically acceptable salts and esters.

47. The method of claim 32 wherein said light energy is applied at a level that does not change the treatment site temperature.

48. The method of claim 32 further comprising a second therapeutic agent in said composition, and wherein said mechanical energy is applied at a first frequency associated with delivery of said therapeutic agent to said treatment site, and said mechanical energy is then applied at a second frequency associated with delivery of said second therapeutic agent to said treatment site, and wherein said first frequency and said second frequency are different.

49. The method of claim 48 wherein said first frequency and said second frequency are determined by microdialysis of said first therapeutic agent and said second therapeutic agent.

50. The method of claim 48 wherein said mechanical energy is modulated and wherein said light energy is modulated synchronously with said mechanical energy and said modulation is at a first modulation frequency for a first period of time followed by a second modulation frequency for a second period of time.

51. The method of claim 50 wherein said light energy and said mechanical energy are modulated at a third modulation frequency for a third period of time.

52. A method for transdermally delivering a therapeutic agent to a patient's treatment site on the skin comprising:
 (a) increasing the temperature of the treatment site by heating the treatment site by about 0.5 to 2° C.;
 (b) applying mechanical energy the treatment site, said mechanical energy having a frequency selected from the group consisting of (i) a frequency of about 15 kHz to 100 kHz; (ii) a frequency of about 100 kHz to 5 MHz modulated with mechanical energy having a frequency of about 15 kHz to 100 kHz; and (iii) having a frequency of about 10 Hz to 1000 Hz modulated with mechanical energy having a frequency of about 15 kHz to 100 kHz;
 (c) applying light energy to said treatment site; and
 (d) applying a composition comprising a therapeutically effective amount of said therapeutic agent to the treatment site.

53. The method of claim 52 wherein steps (a), (b), (c), and (d) are performed simultaneously.

54. The method of claim 52 wherein said applying mechanical energy step comprises applying mechanical energy having a frequency of about 100 kHz to 5 MHz modulated with mechanical energy having a frequency of about 15 kHz and 100 kHz.

55. The method of claim 54 wherein said applying light energy step comprises applying light having a wavelength between about 600 nm and 1650 nm and modulated with a light modulation frequency that is synchronized with said mechanical energy modulation frequency.

56. The method of claim 52 wherein said applying mechanical energy step comprises applying said mechanical energy at a first modulation frequency for a first period of time followed by a second modulation frequency for a second period of time.

57. The method of claim 52 wherein said light energy is modulated synchronously with said mechanical energy and said modulation is at a first modulation frequency for a first period of time followed by a second modulation frequency for a second period of time.

58. The method of claim 57 wherein said light energy and said mechanical energy are modulated at a third modulation frequency for a third period of time.

59. The method of claim 52 wherein said applying mechanical energy step comprises applying mechanical energy having a frequency of about 10 Hz to 1000 Hz modulated with a mechanical energy having a frequency of about 15 kHz to 100 kHz.

60. The method of claim 59 wherein said applying light energy step comprises applying light having a wavelength between about 600 nm and 1650 nm and modulated with a light modulation frequency that is synchronized with said mechanical energy modulation frequency.

61. The method of claim 52 wherein said applying mechanical energy step comprises applying ultrasound having a frequency of about 100 kHz to 5 MHz modulated with a ultrasonic modulation frequency of about 15 kHz and 100 kHz.

62. The method of claim 61 wherein said applying light energy step comprises applying light having a wavelength between about 600 nm and 1650 nm and modulated with a light modulation frequency that is synchronized with said ultrasonic modulation frequency.

63. The method of claim 52 where said light energy is provided by a light emitting diode or scanning laser.

64. The method claim 52 wherein said light energy has a wavelength between about 600 nm and 650 nm and an energy density of about 1 to 20 $J/cm^2$.

65. The method of claim 52 wherein said mechanical energy is provided by an ultrasonic transducer, motor having an offset cam, voice coil, buzzer, or magnetic transducer.

66. The method of claim 52 wherein said therapeutic agent is ascorbic acid or its pharmaceutically acceptable salts and esters.

67. The method of claim 52 wherein said light energy is applied at a level that causes the increase in temperature from about 0.5 to 2° C. at the treatment site.

68. The method of claim 52 further comprising a second therapeutic agent in said composition, and wherein said mechanical energy is applied at a first frequency associated with delivery of said therapeutic agent to said treatment site, and said mechanical energy is then applied at a second frequency associated with delivery of said second therapeutic agent to said treatment site, and wherein said first frequency and said second frequency are different.

69. The method of claim 68 wherein said first frequency and said second frequency are determined by microdialysis of said first therapeutic agent and said second therapeutic agent.

70. The method of claim 68 wherein said mechanical energy is modulated and wherein said light energy is modulated synchronously with said mechanical energy and said modulation is at a first modulation frequency for a first period of time followed by a second modulation frequency for a second period of time.

71. The method of claim 70 wherein said light energy and said mechanical energy are modulated at a third modulation frequency for a third period of time.

72. A method for transdermally delivering a therapeutic agent to a patient's treatment site on the skin comprising:
 (a) increasing the temperature of the treatment site by heating the treatment site by about 2 to 4° C.;
 (b) applying mechanical energy the treatment site, said mechanical energy having a frequency selected from the group consisting of (i) a frequency of about 15 kHz to 100 kHz; (ii) a frequency of about 100 kHz to 5 MHz modulated with mechanical energy having a frequency of about 15 kHz to 100 kHz; and (iii) a frequency of about 10 Hz to 1000 Hz modulated with mechanical energy having a frequency of about 15 kHz to 100 kHz;
 (c) applying light energy to said treatment site; and
 (d) applying a composition comprising a therapeutically effective amount of said therapeutic agent to the treatment site.

73. The method of claim 72 wherein steps (a), (b), (c), and (d) are performed simultaneously.

74. The method of claim 72 wherein said applying mechanical energy step comprises applying mechanical energy having a frequency of about 100 kHz to 5 MHz modulated with mechanical energy having a frequency of about 15 kHz and 100 kHz.

75. The method of claim 74 wherein said applying light energy step comprises applying light having a wavelength between about 600 nm and 1650 nm and modulated with a light modulation frequency that is synchronized with said mechanical energy modulation frequency.

76. The method of claim 72 wherein said applying mechanical energy step comprises applying said mechanical energy at a first modulation frequency for a first period of time followed by a second modulation frequency for a second period of time.

77. The method of claim 72 wherein said light energy is modulated synchronously with said mechanical energy and said modulation is at a first modulation frequency for a first period of time followed by a second modulation frequency for a second period of time.

78. The method of claim 77 wherein said light energy and said mechanical energy are modulated at a third modulation frequency for a third period of time.

79. The method of claim 72 wherein said applying mechanical energy step comprises applying mechanical energy having a frequency of about 10 Hz to 1000 Hz modulated with a mechanical energy having a frequency of about 15 kHz to 100 kHz.

80. The method of claim 79 wherein said applying light energy step comprises applying light having a wavelength between about 600 nm and 1650 nm and modulated with a light modulation frequency that is synchronized with said mechanical energy modulation frequency.

81. The method of claim 72 wherein said applying mechanical energy step comprises applying ultrasound having a frequency of about 100 kHz to 5 MHz modulated with a ultrasonic modulation frequency of about 15 kHz to 100 kHz.

82. The method of claim 81 wherein said applying light energy step comprises applying light having a wavelength between about 600 nm and 1650 nm and modulated with a light modulation frequency that is synchronized with said ultrasonic modulation frequency.

83. The method of claim 72 where said light energy is provided by a light emitting diode or scanning laser.

84. The method claim 72 wherein said light energy has a wavelength between about 600 nm and 650 nm and an energy density of about 1 to 20 J/cm$^2$.

85. The method of claim 72 wherein said mechanical energy is provided by an ultrasonic transducer, motor having an offset cam, voice coil, buzzer, or magnetic transducer.

86. The method of claim 72 wherein said therapeutic agent is ascorbic acid or its pharmaceutically acceptable salts and esters.

87. The method of claim 72 wherein said light energy is applied at a level that causes the increase in temperature from about 0.5 to 2° C. at the treatment site.

88. The method of claim 72 further comprising a second therapeutic agent in said composition, and wherein said mechanical energy is applied at a first frequency associated with delivery of said therapeutic agent to said treatment site, and said mechanical energy is then applied at a second frequency associated with delivery of said second therapeutic agent to said treatment site, and wherein said first frequency and said second frequency are different.

89. The method of claim 88 wherein said first frequency and said second frequency are determined by microdialysis of said first therapeutic agent and said second therapeutic agent.

90. The method of claim 88 wherein said mechanical energy is modulated and wherein said light energy is modulated synchronously with said mechanical energy and said modulation is at a first modulation frequency for a first period of time followed by a second modulation frequency for a second period of time.

91. The method of claim 90 wherein said light energy and said mechanical energy are modulated at a third modulation frequency for a third period of time.

* * * * *